(12) United States Patent
Rebellino et al.

(10) Patent No.: US 12,721,608 B2
(45) Date of Patent: Sep. 1, 2026

(54) SAMPLE MANAGEMENT FOR CORE NEEDLE BIOPSY DEVICE

(71) Applicant: Devicor Medical Products, Inc., Cincinnati, OH (US)

(72) Inventors: Justin Rebellino, Cincinnati, OH (US); David C. McBreen, Cincinnati, OH (US); Andrew P. Nock, Dayton, OH (US); Jessica P. Leimbach, Cincinnati, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 925 days.

(21) Appl. No.: 17/719,657

(22) Filed: Apr. 13, 2022

(65) Prior Publication Data

US 2022/0313227 A1 Oct. 6, 2022

Related U.S. Application Data

(63) Continuation of application No. PCT/US2020/055779, filed on Oct. 15, 2020.

(Continued)

(51) Int. Cl.

*A61B 10/00* (2006.01)
*A61B 10/02* (2006.01)

(52) U.S. Cl.

CPC ...... *A61B 10/0096* (2013.01); *A61B 10/0275* (2013.01); *A61B 2010/0225* (2013.01)

(58) Field of Classification Search

CPC ........... A61B 10/0275; A61B 10/0208; A61B 10/0266; A61B 10/0225; A61B 10/0096;

(Continued)

(56) References Cited

U.S. PATENT DOCUMENTS 5,511,556 A 4/1996 DeSantis
5,526,822 A 6/1996 Burbank et al.

(Continued)

FOREIGN PATENT DOCUMENTS

EP 3103397 12/2016
EP 3103397 A1 * 12/2016 ......... A61B 10/0096

(Continued)

OTHER PUBLICATIONS

International Search Report and Written Opinion dated May 21, 2021 for Application No. PCT/US2020/055779, 17 pages.

(Continued)

*Primary Examiner* — Patrick Fernandes
*Assistant Examiner* — Shawn Curtis Broughton
(74) *Attorney, Agent, or Firm* — FBT Gibbons LLP

(57) ABSTRACT

A core needle biopsy device includes a needle assembly, a drive assembly, and a tissue sample holder. The needle assembly includes a piercer and a hollow cutter. The piercer includes a sharp distal tip and a notch proximal to the distal tip. The piercer is slidably disposed within the cutter to sever a tissue sample into the notch of the piercer. The drive assembly is configured to selectively move the piercer and the cutter. The tissue sample holder has a sample chamber and a wiper. The wiper is movable relative to the piercer and cutter to manipulate a severed tissue sample into the sample chamber.

20 Claims, 27 Drawing Sheets

Related U.S. Application Data

(60) Provisional application No. 62/916,277, filed on Oct. 17, 2019.

(58) Field of Classification Search
CPC ... A61B 10/0233; A61B 5/6848; A61B 90/39; A61B 18/1477
See application file for complete search history.

(56) References Cited

U.S. PATENT DOCUMENTS

| | | | |
|---|---|---|---|
| 5,560,373 | A | 10/1996 | DeSantis |
| 5,817,033 | A | 10/1998 | DeSantis et al. |
| 5,971,939 | A | 10/1999 | DeSantis et al. |
| 6,086,544 | A | 7/2000 | Hibner et al. |
| 6,162,187 | A | 12/2000 | Buzzard et al. |
| 6,432,065 | B1 | 8/2002 | Burdorff et al. |
| 6,752,768 | B2 | 6/2004 | Burdorff et al. |
| 7,442,171 | B2 | 10/2008 | Stephens et al. |
| 7,854,706 | B2 | 12/2010 | Hibner |
| 7,914,464 | B2 | 3/2011 | Burdorff et al. |
| 7,938,786 | B2 | 5/2011 | Ritchie et al. |
| 8,083,687 | B2 | 12/2011 | Parihar |
| 8,118,755 | B2 | 2/2012 | Hibner et al. |
| 8,206,316 | B2 | 6/2012 | Hibner et al. |
| 8,282,574 | B2 | 10/2012 | Coonahan et al. |
| 8,485,989 | B2 | 7/2013 | Videbaek |
| 8,486,989 | B2 | 7/2013 | Videbaek |
| 8,702,623 | B2 | 4/2014 | Parihar et al. |
| 8,858,465 | B2 | 10/2014 | Fiebig |
| 9,326,755 | B2 | 5/2016 | Fiebig et al. |
| 10,368,849 | B2 | 8/2019 | Coonahan et al. |
| 11,013,499 | B2 | 5/2021 | Shabaz |
| 2005/0215921 | A1 | 9/2005 | Hibner et al. |
| 2006/0074345 | A1 | 4/2006 | Hibner |
| 2009/0131821 | A1 | 5/2009 | Speeg et al. |
| 2010/0152610 | A1 | 6/2010 | Parihar et al. |
| 2010/0160819 | A1 | 6/2010 | Parihar et al. |
| 2013/0324882 | A1 | 12/2013 | Mescher |
| 2015/0223787 | A1 | 8/2015 | Coonahan et al. |
| 2019/0231325 | A1 | 8/2019 | Nock |
| 2019/0321009 | A1 | 10/2019 | Nevo et al. |
| 2021/0153850 | A1 * | 5/2021 | Kjeldsen ............ A61B 10/0096 |

FOREIGN PATENT DOCUMENTS

| | | |
|---|---|---|
| EP | 3578111 | 12/2019 |
| EP | 3669789 | 6/2020 |
| JP | 6028039 A | 11/2016 |
| WO | WO 2018/087367 | 5/2018 |
| WO | WO 2018/127848 | 7/2018 |

OTHER PUBLICATIONS

Canadian Office Action dated Nov. 3, 2023 for Application No. 3,155,683, 9 pages.

Canadian Office Action dated Aug. 29, 2024 for Application No. 3,155,683, 8 pages.

Chinese Office Action dated Mar. 24, 2025 for Application No. 202080069346.0, 7 pages.

European Communication dated Aug. 3, 2023 for Application No. 20828586.6, 7 pages.

European Communication dated Feb. 20, 2025 for Application No. 20828586.6, 8 pages.

Japanese Office Action dated Jul. 2, 2024 for Application No. 2022-522910, 14 pages.

Korean Office Action dated Apr. 29, 2025 for Application No. 10-2022-522910, 7 pages.

Korean Office Action dated Jan. 6, 2026 for Application No. 10-2022-701163, 6 pages.

* cited by examiner 30
32
52
53
46
50
54
22
44
40
20
43
42
26
24

210
212
218
220
213
214
222
216

244
242
250
254
252
246
246
240
246
254
250
252

SAMPLE MANAGEMENT FOR CORE NEEDLE BIOPSY DEVICE

PRIORITY

This application is a continuation of International Application Number PCT/US2020/055779, filed on Oct. 15, 2020, which claims priority to U.S. Provisional Application Ser. No. 62/916,277 entitled "Sample Management for Core Needle Biopsy Device," filed on Oct. 17, 2019, the disclosures of which are incorporated by reference herein.

BACKGROUND

A biopsy is the removal of a tissue sample from a patient to enable examination of the tissue for signs of cancer or other disorders. Tissue samples may be obtained in a variety of ways using various medical procedures involving a variety of the sample collection devices. For example, biopsies may be open procedures (surgically removing tissue after creating an incision) or percutaneous procedures (e.g. by fine needle aspiration, core needle biopsy, or vacuum assisted biopsy). After the tissue sample is collected, the tissue sample is typically analyzed at a lab (e.g. a pathology lab, biomedical lab, etc.) that is set up to perform the appropriate tests (such as histological analysis).

Biopsy samples have been obtained in a variety of ways in various medical procedures including open and percutaneous methods using a variety of devices. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

One technique for collecting a breast biopsy is to use a core needle biopsy device. One such device is the MAX-CORE disposable core biopsy instrument manufactured by Bard Biopsy Systems. Core needle biopsy devices frequently use a sharp, solid piercer equipped with a lateral tissue receiving notch positioned adjacent to the distal end of the piercer. When tissue is received within the notch, an elongate hollow cutting sheath is translated over the notch to sever a tissue sample. The severed tissue sample is then stored within the notch until both the piercer and the cutting sheath are removed from the patient. Thus, in core-needle biopsy devices, only one tissue sample can be collected per insertion of the piercer and cutting sheath.

In contrast to core needle breast biopsy procedures, vacuum-assisted breast biopsy devices permit the probe to remove multiple samples without requiring the probe be removed from the breast after every sample is collected. For instance, in a vacuum assisted breast biopsy device, a hollow needle is used to penetrate tissue. The hollow needle includes a lateral aperture adjacent to a sharp distal tip. A hollow cutter is disposed within the hollow needle and is moved axially relative to the lateral aperture of the needle to sever tissue samples. Once a tissue sample is severed by the hollow cutter, the tissue sample is transported axially though the cutter and collected in a tissue collection feature.

Examples of vacuum assisted biopsy devices and biopsy system components are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pat. No. 6,162,187, entitled "Fluid Collection Apparatus for a Surgical Device," issued Dec. 19, 2000; U.S. Pat. No. 6,432,065, entitled "Method for Using a Surgical Biopsy System with Remote Control for Selecting an Operational Mode," issued Aug. 13, 2002; U.S. Pat. No. 6,752,768, entitled "Surgical Biopsy System with Remote Control for Selecting an Operational Mode," issued Jun. 22, 2004; U.S. Pat. No. 7,442,171, entitled "Remote Thumbwheel for a Surgical Biopsy Device," issued Oct. 8, 2008; U.S. Pat. No. 7,854,706, entitled "Clutch and Valving System for Tetherless Biopsy Device," issued Dec. 1, 2010; U.S. Pat. No. 7,914,464, entitled "Surgical Biopsy System with Remote Control for Selecting an Operational Mode," issued Mar. 29, 2011; U.S. Pat. No. 7,938,786, entitled "Vacuum Timing Algorithm for Biopsy Device," issued May 10, 2011; U.S. Pat. No. 8,083,687, entitled "Tissue Biopsy Device with Rotatably Linked Thumbwheel and Tissue Sample Holder," issued Dec. 21, 2011; U.S. Pat. No. 8,118,755, entitled "Biopsy Sample Storage," issued Feb. 1, 2012; U.S. Pat. No. 8,206,316, entitled "Tetherless Biopsy Device with Reusable Portion," issued on Jun. 26, 2012; U.S. Pat. No. 8,702,623, entitled "Biopsy Device with Discrete Tissue Chambers," issued on Apr. 22, 2014; U.S. Pat. No. 8,858,465, entitled "Biopsy Device with Motorized Needle Firing," issued Oct. 14, 2014; and U.S. Pat. No. 9,326,755, entitled "Biopsy Device Tissue Sample Holder with Bulk Chamber and Pathology Chamber," issued May 3, 2016. The disclosure of each of the above-cited U.S. Patents is incorporated by reference herein.

Additional examples of vacuum assisted biopsy devices and biopsy system components are disclosed in U.S. Pub. No. 2006/0074345, entitled "Biopsy Apparatus and Method," published Apr. 6, 2006 and now abandoned; U.S. Pub. No. 2009/0131821, entitled "Graphical User Interface for Biopsy System Control Module," published May 21, 2009, now abandoned; U.S. Pub. No. 2010/0152610, entitled "Hand Actuated Tetherless Biopsy Device with Pistol Grip," published Jun. 17, 2010, now abandoned; U.S. Pub. No. 2010/0160819, entitled "Biopsy Device with Central Thumbwheel," published Jun. 24, 2010, now abandoned; and U.S. Pub. No. 2013/0324882, entitled "Control for Biopsy Device," published Dec. 5, 2013. The disclosure of each of the above-cited U.S. Patent Applications Publications is incorporated by reference herein.

Exemplary core needle biopsy devices are disclosed in U.S. Pat. No. 5,560,373, entitled "Needle Core Biopsy Instrument with Durable or Disposable Cannula Assembly," issued on Oct. 1, 1996; U.S. Pat. No. 5,817,033, entitled "Needle Core Biopsy Device," issued on Oct. 6, 1998; U.S. Pat. No. 5,971,939, entitled "Needle Core Biopsy Device," issued on Oct. 26, 1999; and U.S. Pat. No. 5,511,556, entitled "Needle Core Biopsy Instrument," issued on Apr. 30, 1996. The disclosure of each of the above-cited U.S. Patents is incorporated by reference herein.

In some examples, it may be desirable to combine features from a core needle biopsy device and a vacuum assisted biopsy device to obtain the advantage of both devices and also reduce the overall disadvantages. For instance, core needle biopsy devices may be advantageous for their simplicity, light weight, and maneuverability. Furthermore, core needle biopsy devices generally include smaller gauge needles, which can be desirable to increase patient comfort and recovery times. Meanwhile, vacuum assisted biopsy devices may be advantageous for their ability to collect multiple samples in a single insertion. Thus, a simple and light weight biopsy device capable of collecting multiple samples with a single insertion may be desirable.

One challenge in the biopsy device configuration described above is management of tissue samples once they are collected using the biopsy device. Challenges can arise due to the unique needle and cutter configuration that is encountered in the context of core needle biopsy devices. For instance, the cutter can be on the exterior of an inner piercer, stylet, or needle. A notch in the inner piercer can then be used to transport a severed tissue sample through the cutter. While the use of the notch can improve sample acquisition, collection of the severed tissue sample from the notch can be challenging due to the size and/or shape of the notch as well as the characteristics of the severed tissue sample (e.g., "sticky" or "clingy"). Thus, certain tissue sample collection features may be desirable for integration into a biopsy device that combines features of core needle biopsy devices and vacuum assisted biopsy devices.

While several systems and methods have been made and used for obtaining a biopsy sample, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

Figure 1:
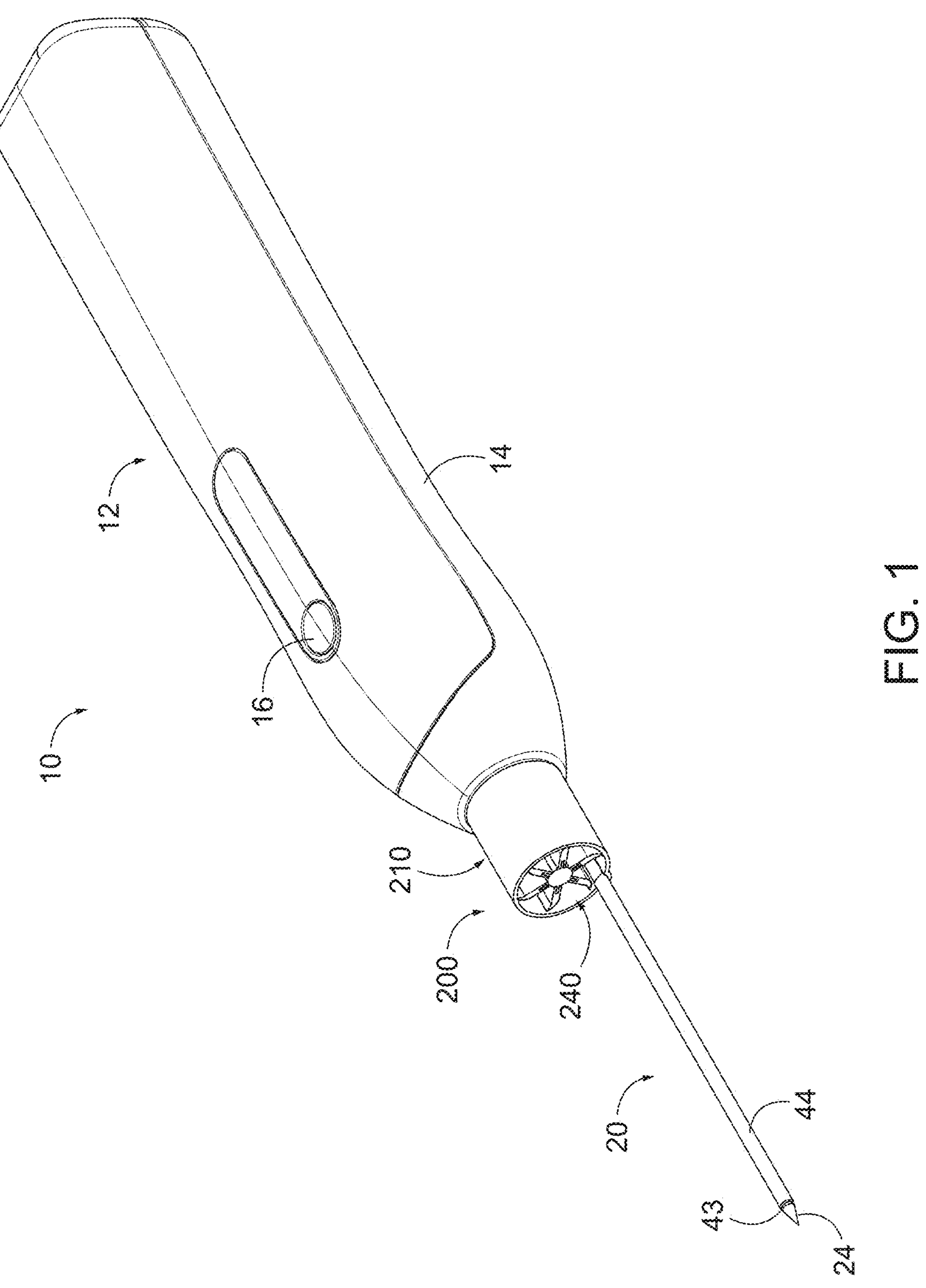
FIG. 1 depicts a perspective view of an exemplary core needle biopsy device.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Biopsy devices may be used to collect tissue samples in a variety of ways. For example, in some instances tissue samples are collected into a single tissue basket such that all tissue samples collected during a given biopsy procedure are deposited into the single tissue sample basket. In some other instances, tissue samples are collected into a tissue sample holder having separate compartments for each collected tissue sample. Such a multi-compartment tissue sample holder may additionally include trays or strips that individually hold each tissue sample separately from the other tissue samples. Such trays or strips may be removable or otherwise separable from the tissue sample holder at the conclusion of a biopsy procedure.

Regardless of the structure in which the tissue samples are stored, tissue samples may be collected using biopsy devices under the guidance of various imaging modalities such as ultrasound image guidance, stereotactic (X-ray) guidance, MRI guidance, Positron Emission Mammography ("PEM" guidance), Breast-Specific Gamma Imaging ("BSGI") guidance, or otherwise. Each procedure has its own methodology based on the form of imaging guidance used.

Vacuum assisted biopsy devices and core needle biopsy devices both may have various advantages over the other, depending on context. For instance, one advantage of vacuum assisted biopsy devices is that vacuum assistance permits removal of multiple tissue samples using a single insertion. However, while core needle biopsy devices lack this feature, use of core needle biopsy devices may still be desirable. For instance, core needle biopsy devices are generally capable of having smaller needles relative to core needle biopsy devices, thereby reducing patient anxiety and increasing the capacity of the needle to penetrate a lesion. Therefore, in some instances it may be desirable to incorporate the feature of multiple sample removal of a vacuum assisted biopsy device into a core needle biopsy device to achieve the benefits present in both styles of biopsy device.

A desirable feature of the device described herein, which is a core needle biopsy device is that the device allows for single insertion with multiple samples being obtained whilst using a core needle type device. To facilitate this functionality, the biopsy device further includes a tissue sample holder having one or more features to facilitate collection of a severed tissue sample from a notch, dugout, aperture, and/or other sample collection feature. Currently, it is believed that only vacuum assisted biopsy devices have this ability.

I. Exemplary Core Needle Biopsy Device with Multi-Sample Collection

FIG. 1 shows an exemplary core needle biopsy device (10) for use in a breast biopsy procedure. Core needle biopsy device (10) of the present example comprises a body (12) and a needle assembly (20) extending distally from body (12). Body (12) includes an outer housing (14) and an actuation member (16) disposed on outer housing (14). As will be describe in greater detail below, outer housing (14) encloses various components of biopsy device (10), which are used to drive needle assembly (20) through a cutting cycle and a tissue acquisition cycle. To this end, outer housing (14) of the present example is sized and shaped for grasping by an operator using a single hand Although not shown, it should be understood that in some examples outer housing (14) may comprise multiple parts such that each part interconnects to form outer housing (14).

A. Exemplary Needle Assembly

Figure 2:
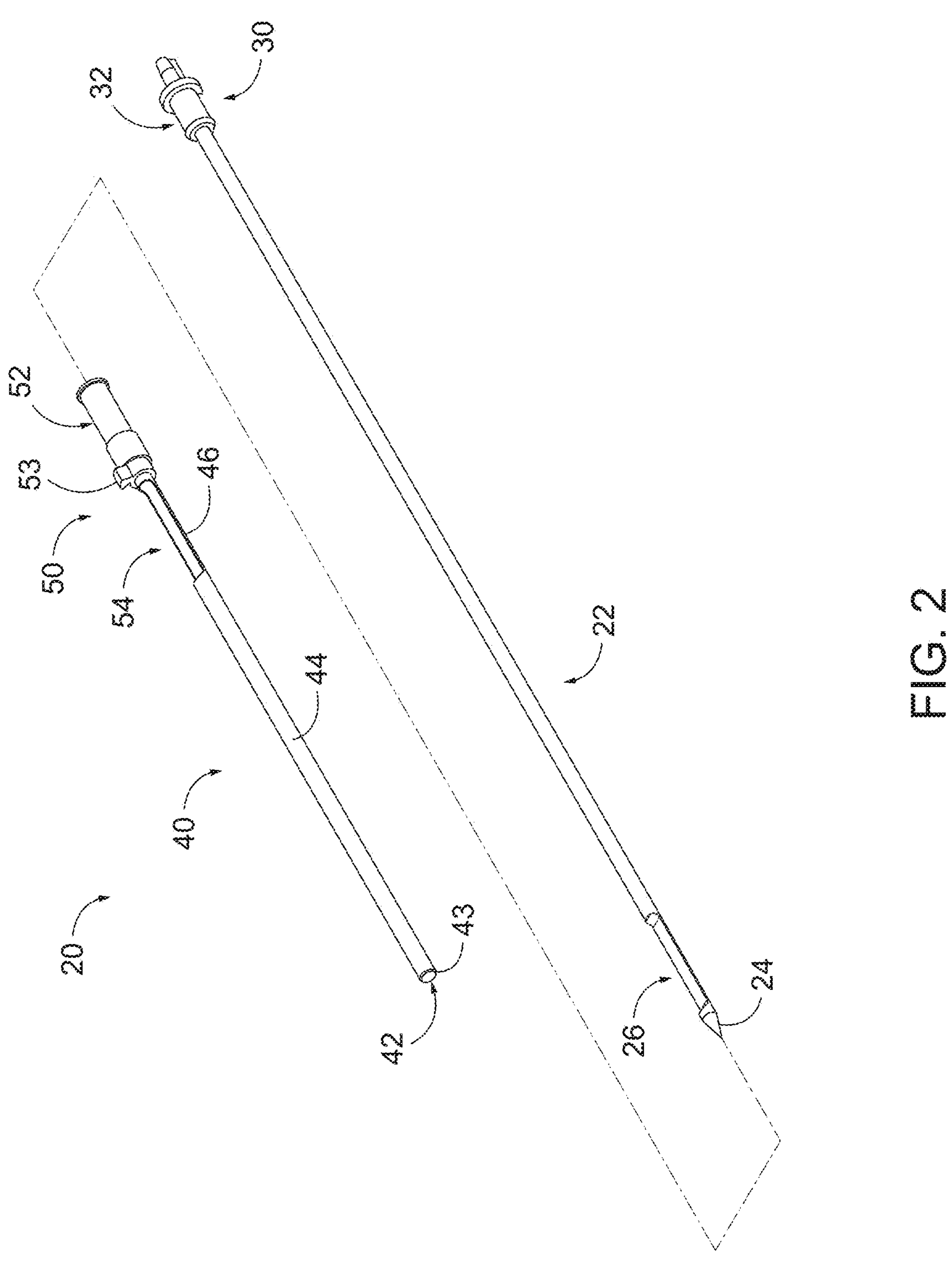
FIG. 2 depicts an exploded view of a needle assembly of the core needle biopsy device of FIG. 1.
Figure 3:
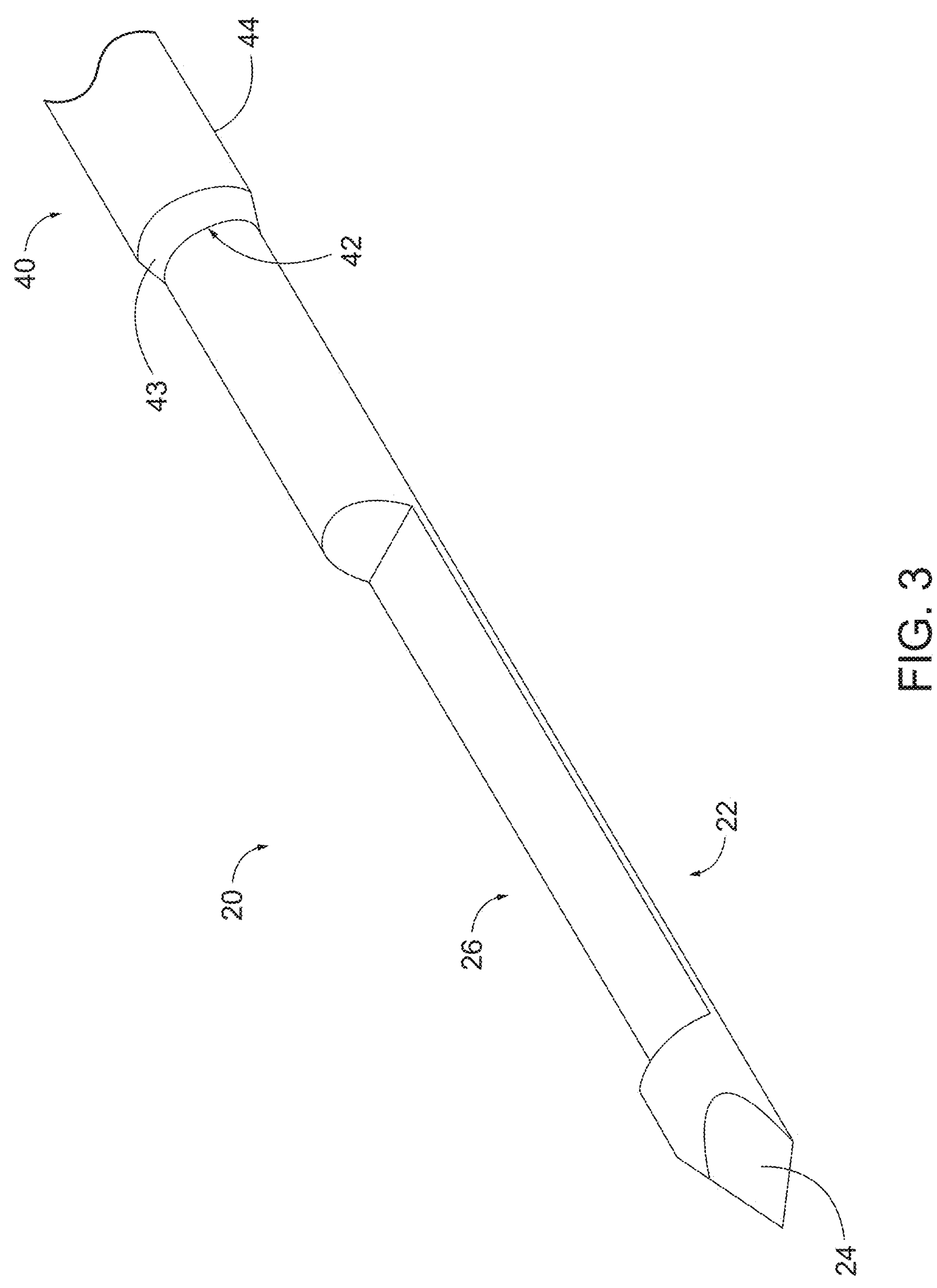
FIG. 3 depicts a perspective view of the needle assembly of FIG. 2.

FIGS. 2 and 3 show needle assembly (20) in greater detail. As can be seen in FIG. 2, needle assembly (20) comprises an elongate piercer (22) and an elongate cutter (40). As will be described in greater detail below, piercer (22) is generally movable relative to cutter (40) to pierce tissue and collect tissue samples, while cutter is generally movable relative to piercer (22) to sever tissue samples. Piercer (22) comprises a generally cylindrical rod having a sharp distal tip (24) and a notch (26) disposed adjacent to distal tip (24). As will be described in greater detail below, distal tip (24) is generally configured to penetrate tissue of a patient. As will also be described in greater detail below, notch (26) is generally configured to receive tissue therein such that a tissue sample may be collected within notch (26) after the tissue sample is severed by cutter (40).

An end portion (30) is disposed on the proximal end of piercer (22). End portion (30) of the present example is overmolded onto the proximal end of piercer (22) and is generally configured to enhance the manipulability of piercer (22). In particular, end portion (30) comprises a receiving feature (32) in the form of a cylindrical indentation or notch. Receiving feature (32) is configured to receive a portion of a piercer drive assembly (300). As will be described in greater detail below, this permits piercer drive assembly (300) to drive movement of piercer (22) through a predetermined sequence of movement.

Cutter (40) comprises a generally hollow cylindrical tube that is configured to receive piercer (22) therein. Cutter (40) comprises an open distal end (42), a cannula portion (44) and an end portion (50). Open distal end (42) is configured to permit at least a portion of piercer (22) to protrude from cutter (40) when piercer (22) is moved relative to cutter (40). As will be described in greater detail below, this configuration permits needle assembly (20) to move through the cutting cycle and the tissue acquisition cycle by permitting notch (26) of piercer (22) to move relative to distal end (42) of cutter (40).

Open distal end (42) of the present example includes a tapered edge (43). Tapered edge (43) is generally configured to slice through tissue to separate tissue samples when cutter (40) is moved relative to notch (26) of piercer (22). Thus, it should be understood that tapered edge (43) is generally configured to act a blade. Although the present example is described and shown as using a tapered configuration, it should be understood that in other examples various alternative configurations can be used. For instance, in some examples tapered edge (43) includes a plurality of serrations in addition or in alternative to the taper shown. In still other examples, tapered edge (43) can include any other additional or alternative cutting surface as will be apparent to those of ordinary skill in the art in view of the teachings herein.

Cannula portion (44) of cutter (40) extends proximally from distal end (42) through end portion (50) such that piercer (22) can be received with the proximal end of cutter (40). Unlike end portion (30) of piercer (22), end portion (50) of cutter (40) is generally elongate such that end portion (50) can accommodate additional features that will be described in greater detail below. In the present example, the distal extension of end portion (50) can be relative to outer housing (14) to permit a portion of end portion (50) to be accessible to an operator for tissue sample collection purposes. Various suitable tissue collection mechanisms associated with end portion (50) will be described in greater detail below.

End portion (50) of cutter (40) comprises a receiving feature (52) and a tissue collection feature (54). As with receiving feature (32) of piercer (22), receiving feature (52) of end portion (50) comprises a cylindrical indentation, slot, or other receiving feature that is configured to receive at least a portion of a cutter drive assembly (200). As will be described in greater detail below, receiving feature (52) is configured to receive at least a portion of cutter drive assembly (200) to permit cutter drive assembly (200) to move cutter (40) through a predetermined sequence of movement.

Tissue collection feature (54) is disposed distally relative to receiving feature (52). Tissue collection feature (54) generally defines an elongate notch that is open to cannula portion (44) of cutter (40). Thus, cannula portion (44) includes a cutout portion (46) that is adjacent to, or otherwise defines, tissue collection feature (54). Accordingly, it should be understood that tissue collection feature (54) is in communication with the hollow interior, or a lumen, defined by cannula portion (44). As will be described in greater detail below, this relationship between tissue collection feature (54) and cannula portion (44) permits an operator to remove tissue samples from cutter (40) as they are collected by piercer (22).

End portion (50) further includes a driver (53) extending outwardly from an outer surface of end portion (50). Driver (53) generally comprises a square or rectangular shape. As will be described in greater detail below, driver (53) is generally configured to manipulate certain features associated with various tissue collection features described herein. Although driver (53) of the present example is shown in connection with end portion (50), it should be understood that in other examples driver (53) can be associated with other components or omitted entirely.

FIG. 3 shows piercer (22) disposed within cutter (40). As can be seen, cutter (40) is generally configured to receive piercer (22) such that piercer (22) is coaxial with cutter (40). In addition, piercer (22) is generally movable relative to open distal end (42) of cutter (40). It should be understood that in some circumstances piercer (22) moves relative to cutter (40), while cutter (40) remains stationary. In other circumstances, cutter (40) moves relative to piercer (22), while piercer (22) remains stationary. In either case, it should be understood that piercer (22) and cutter (40) are generally configured such that notch (26) of piercer (22) moves into and out of cutter (40) such that notch (26) can be disposed distally or proximally relative to open distal end (42) of cutter (40). As will be described in greater detail below, this configuration permits piercer (22) and cutter (40) to operate cooperatively to pierce tissue, cut a tissue sample, and retract the tissue sample for collection by an operator via tissue collection feature (54).

B. Exemplary Drive Assembly

Figure 4:
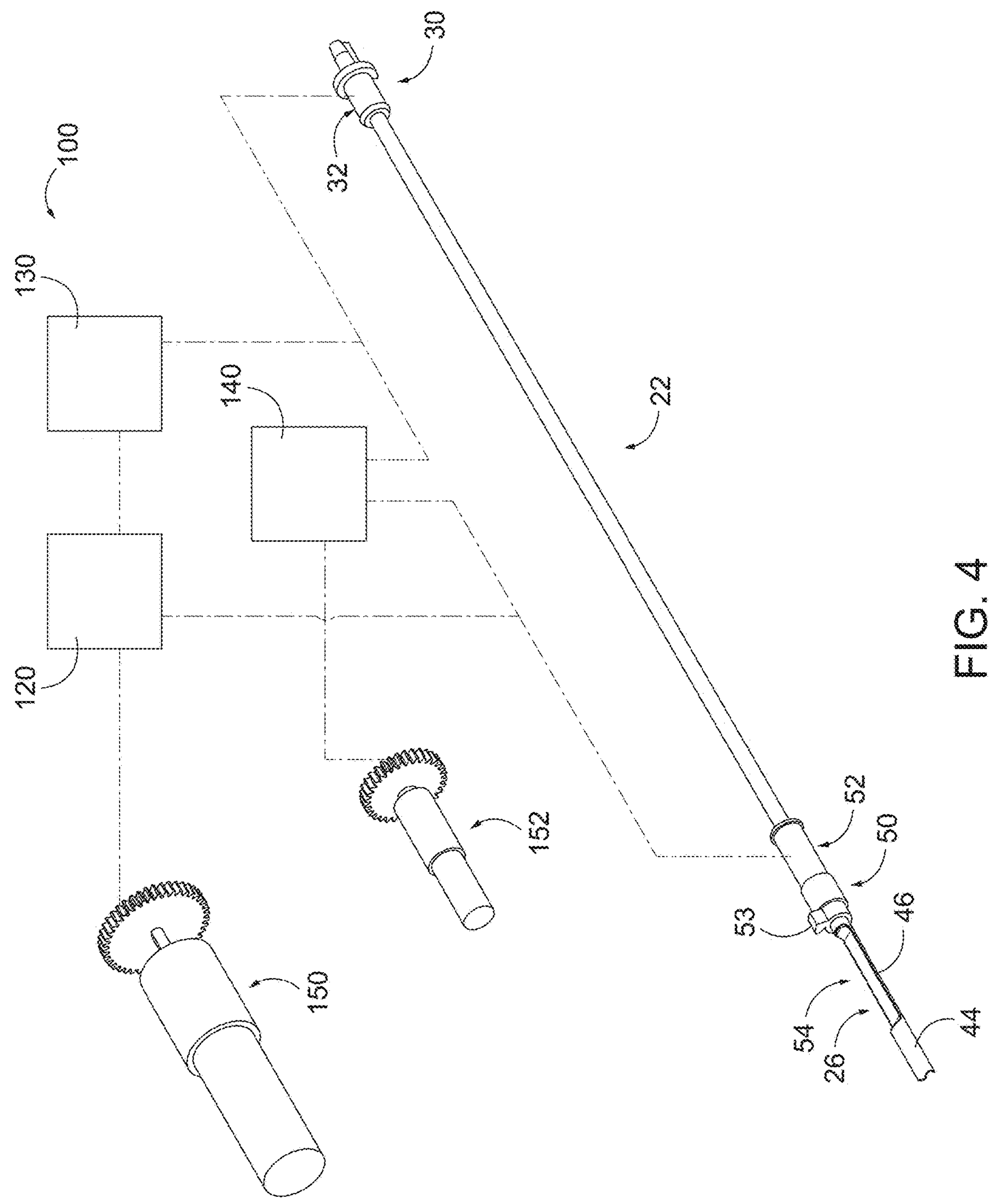
FIG. 4 depicts a perspective view of a drive assembly of the core needle biopsy device of FIG. 1.

FIG. 4 shows the internal components of body (12) of biopsy device (10) with outer housing (14) removed. As can be seen, inside outer housing (14), body (12) includes a drive assembly (100). Drive assembly (100) is generally configured to engage needle assembly (20) to drive piercer (22) and cutter (40) through a predetermined sequence of movements to thereby pierce tissue and acquire a plurality of tissue samples with a single insertion of needle assembly (20) into a patient. Although not shown, it should be understood that outer housing (14) defines various internal geometries that support or otherwise engage drive assembly (100). As will be understood, such internal geometries are used to provide relative movement of various components of drive assembly (100) relative to other components of drive assembly (100) and/or outer housing (14).

Drive assembly (100) comprises a cutter drive assembly (120), a piercer drive assembly (130), and a firing assembly (140). Generally, needle firing assembly (140) is configured to cock and fire cutter (40) and piercer (22) in a predetermined sequence to sever a tissue sample. To collect the severed tissue sample, cutter drive assembly (120) is generally configured to retract cutter (40). Similarly, piercer drive assembly (130) is generally configured to retract piercer (22). It should be understood that, in some examples, both cutter drive assembly (120) and piercer drive assembly (130) can be configured to rotate cutter (40) and/or piercer (22), respectively.

Needle firing assembly (140) is generally shown schematically in the present example. Thus, it should be understood that in some examples needle firing assembly (140) can take on a variety of forms having a combination of gears, racks, leadscrews, carriages, springs, and/or etc. Such components of needle firing assembly (140) can generally be configured to rapidly fire cutter (40) and piercer (22) in a predetermined sequence to penetrate tissue. For instance, in some examples, needle firing assembly (140) is configured to rapidly fire piercer (22) distally to penetrate tissue. Needle firing assembly (140) is also configured to rapidly fire cutter (40) distally. The firing of cutter (40) can be either delayed relative to piercer (22) or slower relative to piercer (22) such that notch (26) can be exposed relative to cutter (40). This sequence can permit tissue to enter notch (26), so that it can be severed by subsequent movement of cutter (40). In addition, it should be understood that needle firing assembly (140) can include other components and/or features to permit cocking of cutter (40) and/or piercer (22) prior to firing.

Cutter drive assembly (120) is generally configured to translate and/or rotate cutter (40) either independently of piercer (22) or in concert therewith. For instance, cutter drive assembly (120) can include various combinations gears, racks, leadscrews, carriages, springs, and/or etc. to drive cutter (40) through a predetermined sequence. In one such sequence, cutter (40) is retracted proximally relative to outer housing (14) to prepare cutter (40) for a tissue collection sequence that will be described in additional detail below. In addition, cutter drive assembly (120) can also be configured to rotate cutter (40) in a predetermined sequence to assist with the tissue collection sequence described in greater detail below.

Piercer drive assembly (130) is generally configured to translate and/or rotate piercer (22) either independently of cutter (40) or in concert therewith. For instance, piercer drive assembly (120) can include various combinations of gears, racks, leadscrews, carriages, springs, and/or etc. to drive piercer (22) through a predetermined sequence. In one such sequence, piercer (22) is retracted proximally relative to cutter (40) after severing a tissue sample to retract the tissue sample proximally towards outer housing (14). Once piercer (22) is retracted, the tissue sample can be extracted for collection in the tissue collection sequence described in greater detail below.

In the present example, drive assembly (100) is powered by one or more motors (150, 152). In particular, drive assembly (100) of the present example includes a drive motor (150) and a firing motor (152). Drive motor (150) of the present example is in communication with both cutter drive assembly (120) and piercer drive assembly (130) to provide rotational motion to both assemblies, which ultimately drives translation and/or rotation of both cutter (40) and piercer (22). Similarly, firing motor (152) is in communication with firing assembly (140) to drive firing and/or cocking of cutter (40) and piercer (22). Although drive assembly (100) of the present example includes two motors (150, 152), it should be understood that in other examples any suitable number of motors may be used such as a single motor, or three or more motors. In addition, motors (150, 152) can be configured to drive cutter drive assembly (120), piercer drive assembly (130), and/or firing assembly (140) in various combinations.

Although cutter drive assembly (120), piercer drive assembly (130), and firing assembly (140) of the present example are shown schematically as three separate drive assemblies, it should be understood that in other examples various elements of cutter drive assembly (120), piercer drive assembly (130), and firing assembly (140) can be combined into a single drive assembly or multiple drive assemblies to drive motion of cutter (40) and piercer (22) in accordance with the sequences described herein. In some examples, cutter drive assembly (120), piercer drive assembly (130), and firing assembly (140) can be constructed in accordance with at least some of the teachings of U.S. Ser. No. 16/381,573, entitled "Core Needle Biopsy Device for Collecting Multiple Samples in a Single Insertion," filed on Apr. 11, 2019, the disclosure of which is incorporated by reference herein.

C. Exemplary Tissue Sample Holder

As noted above, in the present example, needle assembly (20) is configured as a core needle-style tissue acquisition assembly that can collect multiple samples using a single insertion. In some examples, each time a tissue sample is collected, the tissue sample can be physically removed from tissue collection feature (54) by an operator and deposited in a separate location (e.g., formalin jar). However, this physical removal may be undesirable in some examples because it can add an additional step to the biopsy procedure, thereby increasing procedure times. Moreover, this physical removal can introduce extra variables into the biopsy procedure by requiring the operator to keep track of collected tissue samples throughout a biopsy procedure. This physical removal can also lead to frequent operator grip changes throughout a biopsy procedure, which is generally undesirable. Physical removal can also be undesirable because physical movement of tissue samples can degrade tissue architecture. Accordingly, in some examples, it may be desirable to include a tissue sample holder or other sample collection mechanism within biopsy device (10) to collect and store tissue samples throughout a biopsy procedure.

Figure 5:
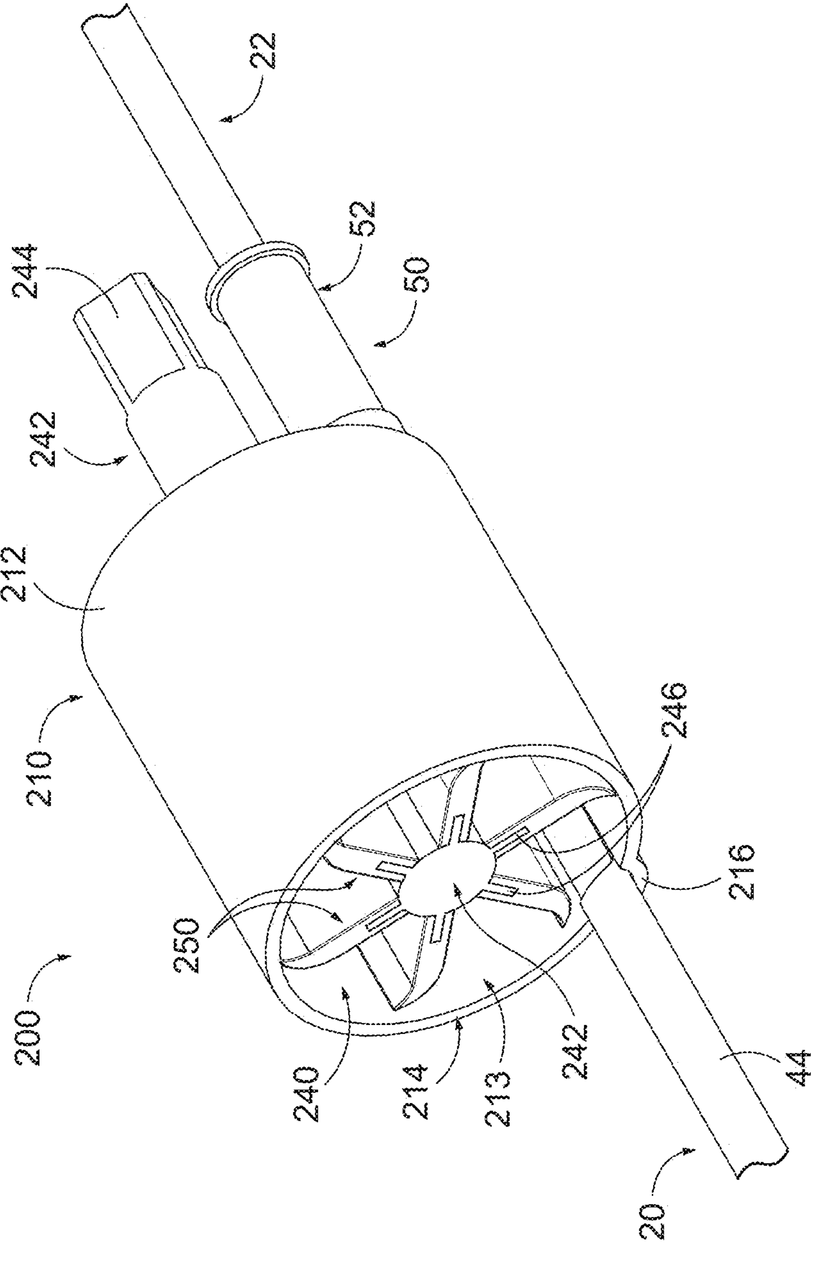
FIG. 5 depicts a perspective view of a tissue sample holder of the core needle biopsy device of FIG. 1.

FIG. 5 shows a tissue sample holder (200) that can be readily used with biopsy device (10) described above. Tissue sample holder (200) of the present example includes an extraction mechanism (240) disposed within a cylindrical outer housing (210). Tissue sample holder (200) is generally configured to collect a plurality of tissue samples from tissue collection feature (54) of needle assembly (20) during a biopsy procedure using rotation of extraction mechanism (240). As will be described in greater detail below, tissue sample holder (200) is generally configured to collect and store six tissue samples, although any suitable number can be collected and stored in other examples.

Figures 6, 7:
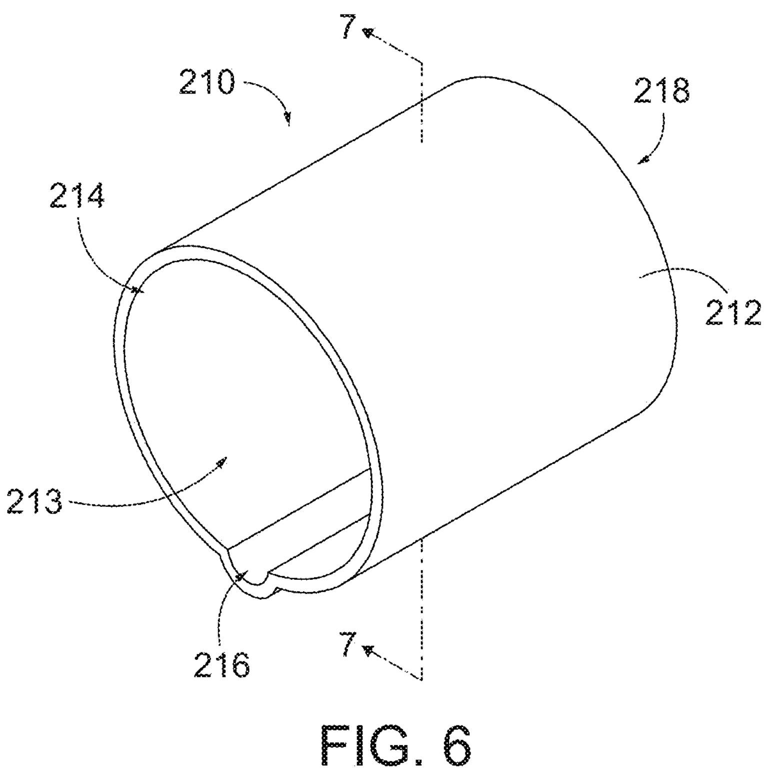
FIG. 6 depicts a perspective view of an outer housing of the tissue sample holder of FIG. 5.
FIG. 7 depicts a side cross-sectional view of the outer housing of FIG. 6, the cross-section taken along line 7-7 of FIG. 6.

FIGS. 6 and 7 show outer housing (210) in greater detail. As can be seen, outer housing (210) includes a cylindrical body (212) defining a sample chamber (213) and an open distal end (214), a closed proximal end (218), and a needle receiving portion (216) extending between the open distal end (214) and the closed proximal end (218). In the present example, outer housing (210) is generally transparent to promote visibility of tissue samples during sample collection. Although outer housing (210) of the present example is shown as having open distal end (214), it should be understood that in other examples, open distal end (214) can be closed or capped to seal sample chamber (213) of outer housing (210) relative to the environment.

Needle receiving portion (216) is generally configured as a semi-cylindrical indentation or bulge in the otherwise cylindrical shape of outer housing (210). Needle receiving portion (216) is generally sized to correspond to the size and shape of needle assembly (20). Thus, needle receiving portion (216) generally defines a pocket or recessed area where needle assembly (20) can rest. As will be described in greater detail below, the particular depth of needle receiving portion (216) can have some relationship to the particular geometric configuration of tissue collection feature (54) of needle assembly (20) to assist with the extraction of a tissue sample from tissue collection feature (54).

Closed proximal end (218) of outer housing (210) includes a shaft bore (220) and a needle bore (222). As will be described in greater detail below, shaft bore (220) is configured to receive rotatable component of extraction mechanism (240) to permit rotation of extraction mechanism (240) from outside outer housing (210). Needle bore (222) is sized to permit needle assembly (20) to pass proximally though closed proximal end (218). Although not shown, it should be understood that either shaft bore (220) and/or needle bore (222) can include seals, O-rings, gaskets, and/or etc. to seal sample chamber (213) of outer housing (210) relative to the environment.

Figure 8:
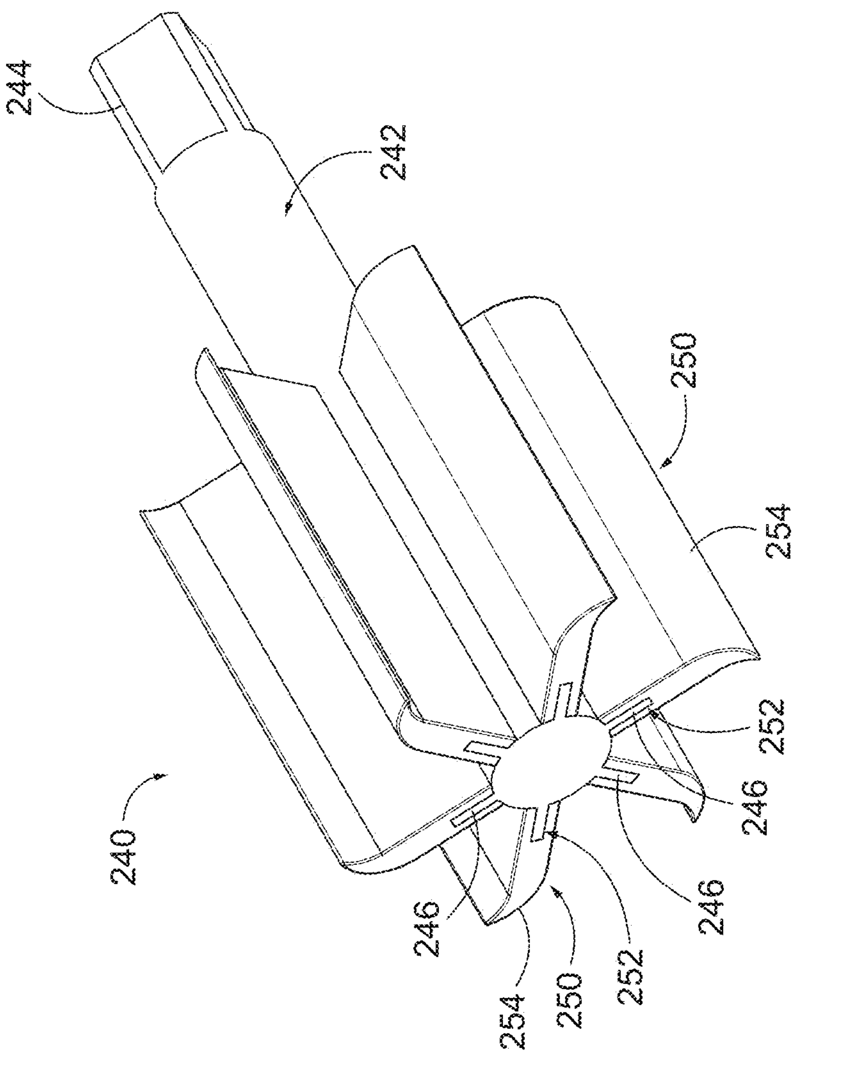
FIG. 8 depicts a perspective view of an extraction mechanism of the tissue sample holder of FIG. 5.

FIG. 8 shows extraction mechanism (240) in greater detail. As can be seen, extraction mechanism (240) includes a shaft (242) and a plurality of wipers (250) arranged around shaft (242). Shaft (242) is generally rotatable to thereby rotate wipers (250) within outer housing (210) to collect and store tissue samples as each tissue sample is collected by needle assembly (20). The proximal end of shaft (242) includes a keyed portion (244) that is configured to communicate with either a manual or motorized driver to rotate shaft (242). Although keyed portion (244) of the present example has a generally square shape, it should be understood that keyed portion (244) can have a variety of configurations suitable to transfer rotary motion such as keys, one or more keyways or channels, a hexagonal shape, a D-shape, and/or etc.

Although not shown, it should be understood that shaft (242) can be driven using keyed portion (244) by a variety of mechanisms. For instance, in some examples, keyed portion (244) is rotatably coupled to any suitable portion of drive assembly (100) such as cutter drive assembly (120), piercer drive assembly (130), firing assembly (140), or some combination thereof. Such a configuration may be desirable to coordinate rotation of shaft (242) with movement of cutter (40) and/or piercer (22). Alternatively, biopsy device (10) can be configured to include an entirely separate drive mechanism for shaft (242). For instance, in some examples, an independent motor can be used to directly power rotation of shaft (242) via a transmission or other drive mechanism. In still other examples, rotation of shaft (242) can be driven by a manual rotation mechanism such as a thumbwheel, pushbutton, or other similar mechanism.

The distal end of shaft (242) includes a plurality of couplers (246) extending outwardly from an exterior surface of shaft (242). Each coupler (246) is generally configured to receive a corresponding wiper (250) to provide a secure base for each wiper to fasten to. Each coupler (246) of the present example defines a generally rectangular cross-section. In other examples, various alternative cross-sectional shapes can be used such as triangular, circular, square, or the like. Although not shown, it should be understood that couplers (246) can extend axially along the length of shaft (242) for a length approximately equivalent to the length of each wiper (250).

Each wiper (250) includes a receiving portion (252) and a tissue manipulation portion (254). Receiving portion (252) has a shape that is complementary to coupler (246) such that receiving portion (252) is configured to receive coupler (246). Accordingly, each receiving portion (252) in the present example defines a generally rectangular shape corresponding to the rectangular shape of each coupler (246). However, it should be understood that in examples where coupler (246) has a different shape, the shape of receiving portion (252) can likewise be changed.

Each manipulation portion (254) defines a generally curved or wave-shaped surface on the outer end of each wiper (250). In the present curved shape, there is a concavity that is oriented in the direction of rotation of shaft (242), The particular shape of each manipulation portion (254) is generally configured to atraumatically engage a tissue sample to manipulate the tissue sample out of tissue collection feature (54) and into sample chamber (213) of outer housing (210). Although each manipulation portion (254) of the present example has a curved shape, it should be understood that in other examples various other shapes can be used such as rounded, square, triangular, and/or etc. In addition, although each manipulation portion (254) is shown as having a generally consistent shape longitudinally, it should be understood that in some examples, the shape can be varied as manipulation portion (254) extends axially. For instance, in some examples each manipulation portion (254) can include one or more slots to enhance fluid management.

Wipers (250) are generally formed of a flexible yet partially resilient material such as rubber or elastomer. For instance, wipers (250) are generally flexible enough to flex around the interface between outer housing (210) and needle assembly (20). This flexibility can be generally desirable to reduce trauma when each wiper (250) engages tissue, while also promoting complete engagement between each wiper (250) and tissue. Meanwhile, at least some resiliency is provided so that each wiper (250) can push or otherwise move a tissue sample. In some examples, the flexibility of each wiper (250) can be characterized in terms of a durometer. Although several suitable durometers can be used, one suitable durometer range is 30 to 80.

Figure 9:
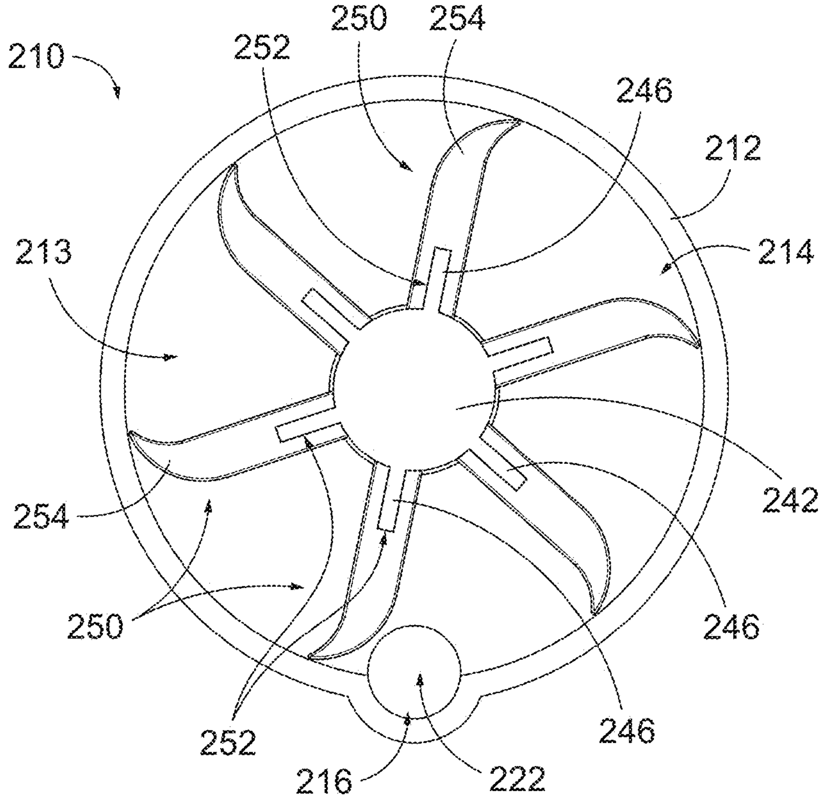
FIG. 9 depicts a front elevational view of the tissue sample holder of FIG. 5.

As best seen in FIG. 9, each coupler (246) and wiper (250) is generally arranged around shaft (242) in an angularly spaced manner such that wipers (250) are spaced equal angular distances from each other. This generally results in couplers (246) and wipers (250) collectively forming a starburst pattern. This configuration may be desirable to divide sample chamber (213) into six equal segments for the storage of tissue samples. However, it should be understood that in other examples, other suitable spacing can be used including unequal spacing.

As also seen in FIG. 9, each wiper (250) extends outwardly relative to coupler (246) away from shaft (242). When extraction mechanism (240) is disposed within outer housing (210), the axial extension of each wiper (250) is such that manipulation portion (254) contacts the inner surface of outer housing (210). Accordingly, it should be understood that each wiper (250) is generally configured to slide along the inner surface of outer housing (210) to sweep one or more tissue samples around inner surface of outer housing (210).

Figure 10A:
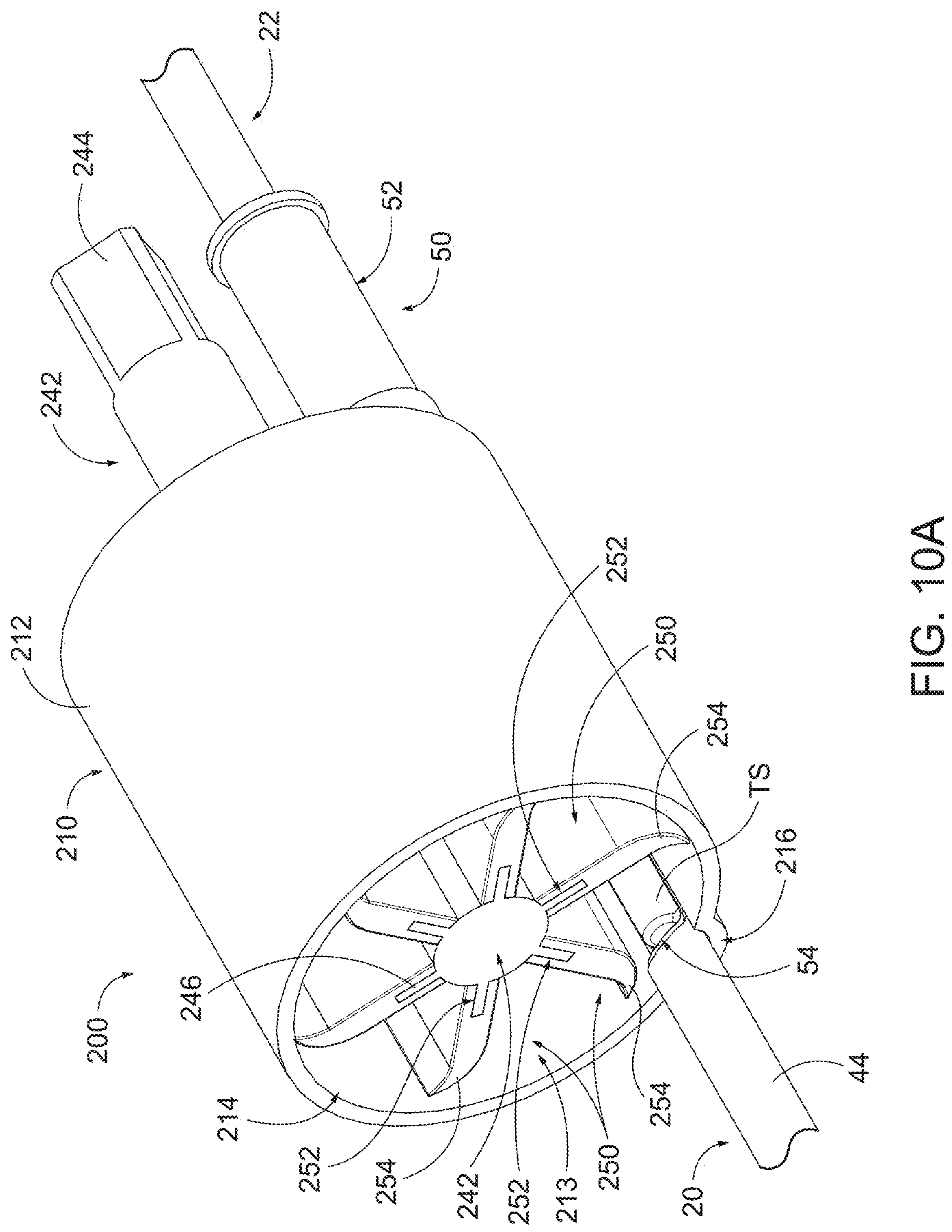
FIG. 10A depicts another perspective view of the tissue sample holder of FIG. 5, with the extraction mechanism positioned to collect a tissue sample.
Figure 10B:
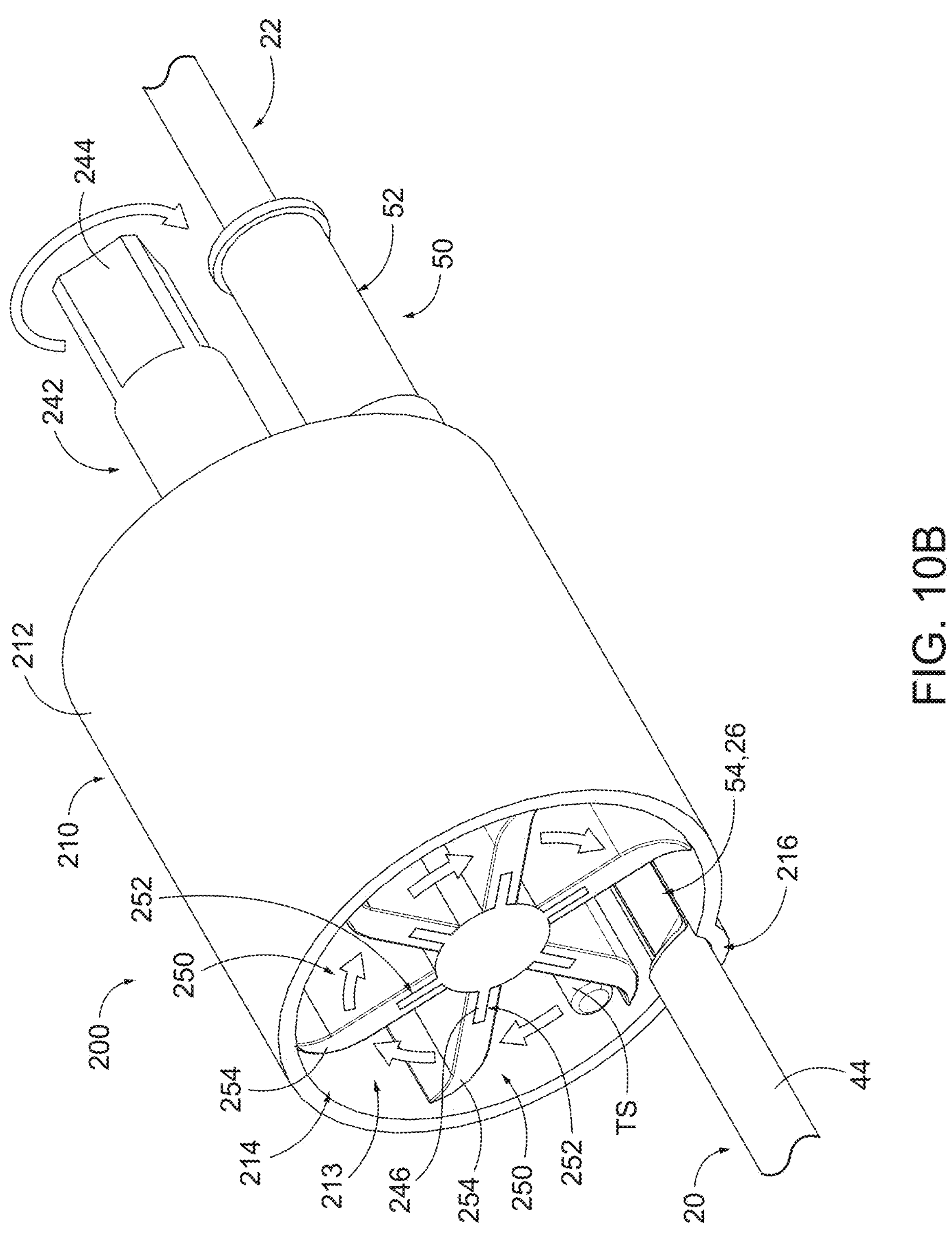
FIG. 10B depicts still another perspective view of the tissue sample holder of FIG. 5, with the extraction mechanism rotated to move the tissue sample.

FIGS. 10A and 10B show an exemplary use of tissue sample holder (200) to collect a tissue sample from needle assembly (20). As can be best seen in FIG. 10A, collection of a tissue sample using tissue sample holder (200) can begin after cutter (40) and piercer (22) have been driven by drive assembly (100) to sever and collect a tissue sample (TS). In particular, once the tissue sample (TS) has been severed, the tissue sample (TS) is transported to tissue collection feature (54) using notch (26) of piercer (22).

In the present example, tissue sample holder (200) is positioned along the axis of needle assembly (20) such that each wiper (250) is aligned with tissue collection feature (54). Accordingly, to collect the tissue sample (TS), shaft (242) can be rotated to rotate each wiper (250) within sample chamber (213) to sweep a selected wiper (250) adjacent to tissue collection feature (54) across notch (26). As the selected wiper (250) sweeps across notch (26), manipulation portion (254) engages the tissue sample (TS) to push the tissue sample (TS) out of tissue collection feature (54).

Once the selected wiper (250) sweeps across notch (26), rotation of shaft can continue as shown in FIG. 10B. Continued rotation results in the tissue sample (TS) being moved around the interior of outer housing (210) to permit the tissue sample (TS) to be stored and ready needle assembly (20) for collection of further tissue samples. At this stage, rotation of shaft (242) can continue in coordination with sequential movement of cutter (40) and piercer (22) for the severing and collection of another tissue sample. Alternatively, rotation of shaft (242) can temporarily cease to permit cutter (40) and piercer (22) to reposition and collect another tissue sample. Regardless, once another tissue sample is collected, rotation of shaft (242) can be used to sweep another wiper (250) across notch (26) to collect another tissue sample. The same process can then be repeated any suitable number of times until tissue sample holder (200) is full or a desired number of tissue samples have been collected.

Figure 11:
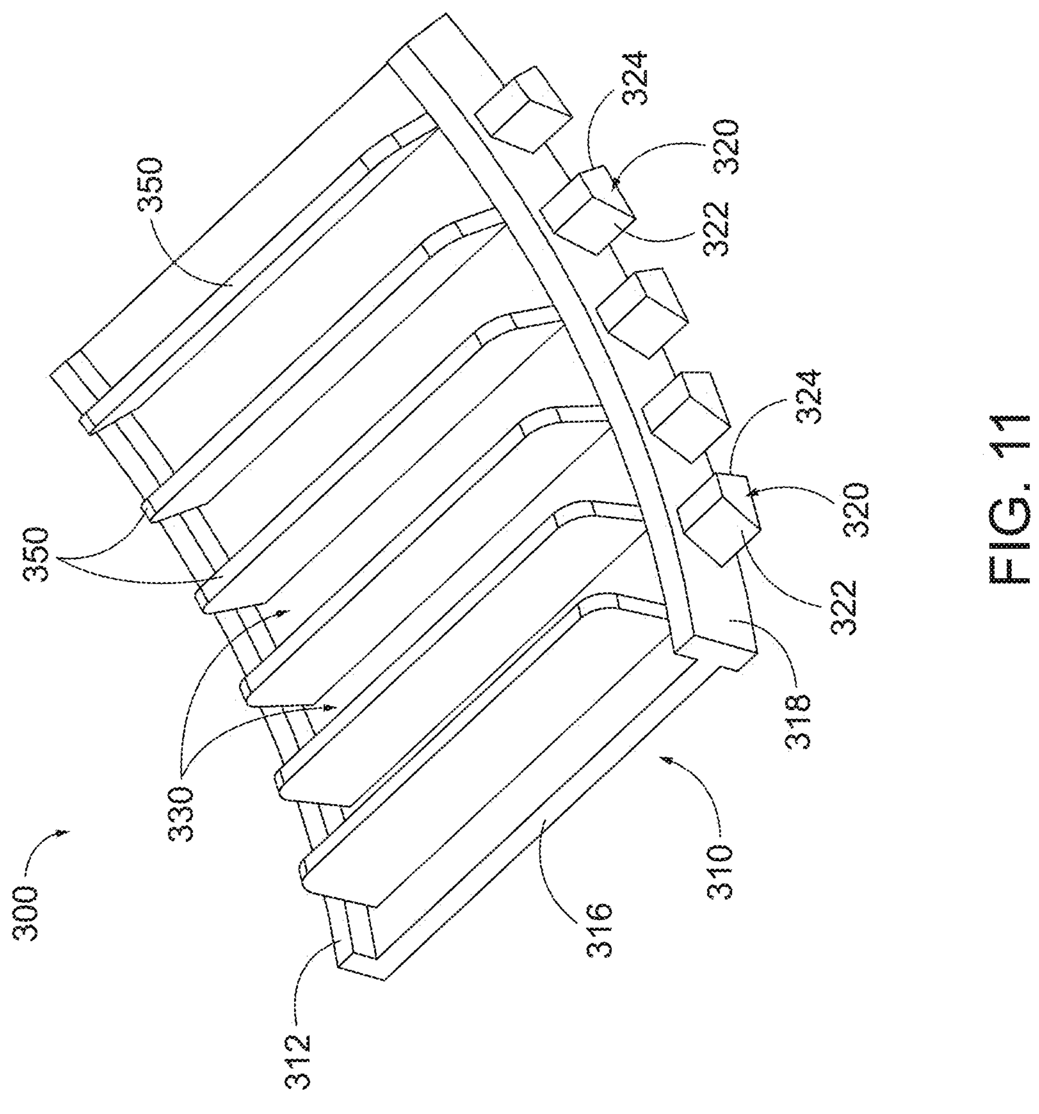
FIG. 11 depicts a perspective view of another exemplary tissue sample holder that can be readily incorporated into the biopsy device of FIG. 1.

II. Exemplary Alternative Tissue Sample Holder with Translatable Lower Wipers FIG. 11 shows another exemplary tissue sample holder (300) that can be readily incorporated into biopsy device (10) described above. Tissue sample holder (300) of the presented example includes a base (310) having a plurality of wipers (350). As with tissue sample holder (200) described above, tissue sample holder (300) of the present example is generally configured to collect a plurality of tissue samples from tissue collection feature (54) of needle assembly (20) during a biopsy procedure. However, unlike tissue sample holder (200) described above, tissue sample holder (300) of the present example configured to be movable by needle assembly (20) for collection of tissue samples from tissue collection feature (54).

Base (310) is best seen in FIG. 11. As can be seen, base (310) generally defines an arcuate shape that defines at least some concavity. Although base (310) of the present example defines an arcuate shape, it should be understood that in other examples, base (310) can define a flat configuration. Base (310) includes a distal wall (312), a proximal wall (318), and a floor (316) extending between distal wall (312) and proximal wall (318). Both proximal wall (318) and distal wall (312) extend upwardly from floor (316). Proximal wall (318) and distal wall (312) further extend longitudinally along the entire length of floor (316). Accordingly, it should be understood that proximal wall (318) and distal wall (312) enclose the proximal end and distal end of floor (316), respectively. As will be described in greater detail below, this enclosure is together used with wipers (350) to define a plurality of sample chambers (330) within body (310).

Distal wall (312), floor (316) and proximal wall (318) are all shown in the present example as having a solid construction. However, it should be understood that in other examples, any of distal wall (312), floor (316), and/or proximal wall (318) can include one or more vents to provide ventilation. For instance, in some examples floor (316) can include a plurality of vent openings or vent slots to provide drainage of fluid during the collection of tissue samples. Suitable vent openings can be generally sized to permit the flow of liquid, while stopping the flow of solid substances such as tissue samples. One or more vents can likewise be disposed in distal wall (312) or proximal wall (318) to further promote drainage of liquid.

Base (310) further includes a plurality of manipulators (320) extending from the proximal face of proximal wall (318). As will be described in greater detail below, each manipulator (320) is generally configured to engage a portion of needle assembly (20) to drive movement of base (310) during tissue collection and thereby index a given sample chamber (330) with tissue collection feature (54). Base (310) of the present example includes five manipulators (320), although any suitable number can be used. For instance, in the present example, each manipulator (320) corresponds to a particular sample chamber (330). Thus, in an example with additional sample chambers (330), additional manipulators (320) can likewise be used.

Each manipulator (320) includes an angled surface (322) and a drive surface (324). Angled surface (322) and drive surface (324) of each manipulator (320) is arranged such that each manipulator (320) forms a shape similar to a wedge. It should be understood that various alternative shapes for each manipulator (320) can be used. For instance, in the present example, the particular geometric shape of each manipulator (320) is generally configured to interact with needle assembly (20) to drive movement of base (310). Thus, in other examples where a different drive mechanism may be used, different manipulator (320) geometries can be used. By way of example only, in some examples, manipulators (320) can be configured as teeth in a rack to engage a gear, pawls, cams, and/or etc.

Wipers (350) are arranged on base (310) to further define each sample chamber (330). In particular, each wiper (350) extends upwardly from floor (316) and is spaced at equal distances from each adjacent wiper (350). Each wiper (350) also extends across floor (316) from distal wall (312) to proximal wall (318). In the present example, six wipers (350) are included to divide the area of floor (316) into five sample chambers (330). However, it should be understood that in other examples various alternative numbers of wipers (350) can be used to form more or less sample chambers (330).

Wipers (350) further extend upwardly beyond the upward extension of distal wall (312) and proximal wall (318). Thus, wipers (350) of the present example are configured to protrude outwardly from base (310). As will be described in greater detail below, this configuration can permit distal wall (312) and proximal wall (318) to ride along a portion of needle assembly (20), while wipers (350) can enter tissue collection feature (54) to extract tissue samples therefrom.

Unlike wipers (250) described above, wipers (350) of the present example have a generally continuous rectangular cross-section configuration with rounded corners. However, it should be understood that wipers (350) are still generally configured to engage with tissue collection feature (54) to remove tissue samples therefrom. Thus, it should be understood that wipers (350) are generally formed of a flexible yet partially resilient material such as rubber or elastomer. As similarly described above, wipers (350) are generally flexible enough to flex around features of needle assembly (20). This flexibility can be generally desirable to reduce trauma when each wiper (350) engages tissue, while also promoting complete engagement between each wiper (350) and tissue. Meanwhile, at least some resiliency is provided so that each wiper (350) can push or otherwise move a tissue sample. In some examples, the flexibility of each wiper (350) can be characterized in terms of a durometer. Although several suitable durometers can be used, one suitable durometer range is 30 to 80.

Figure 12A:
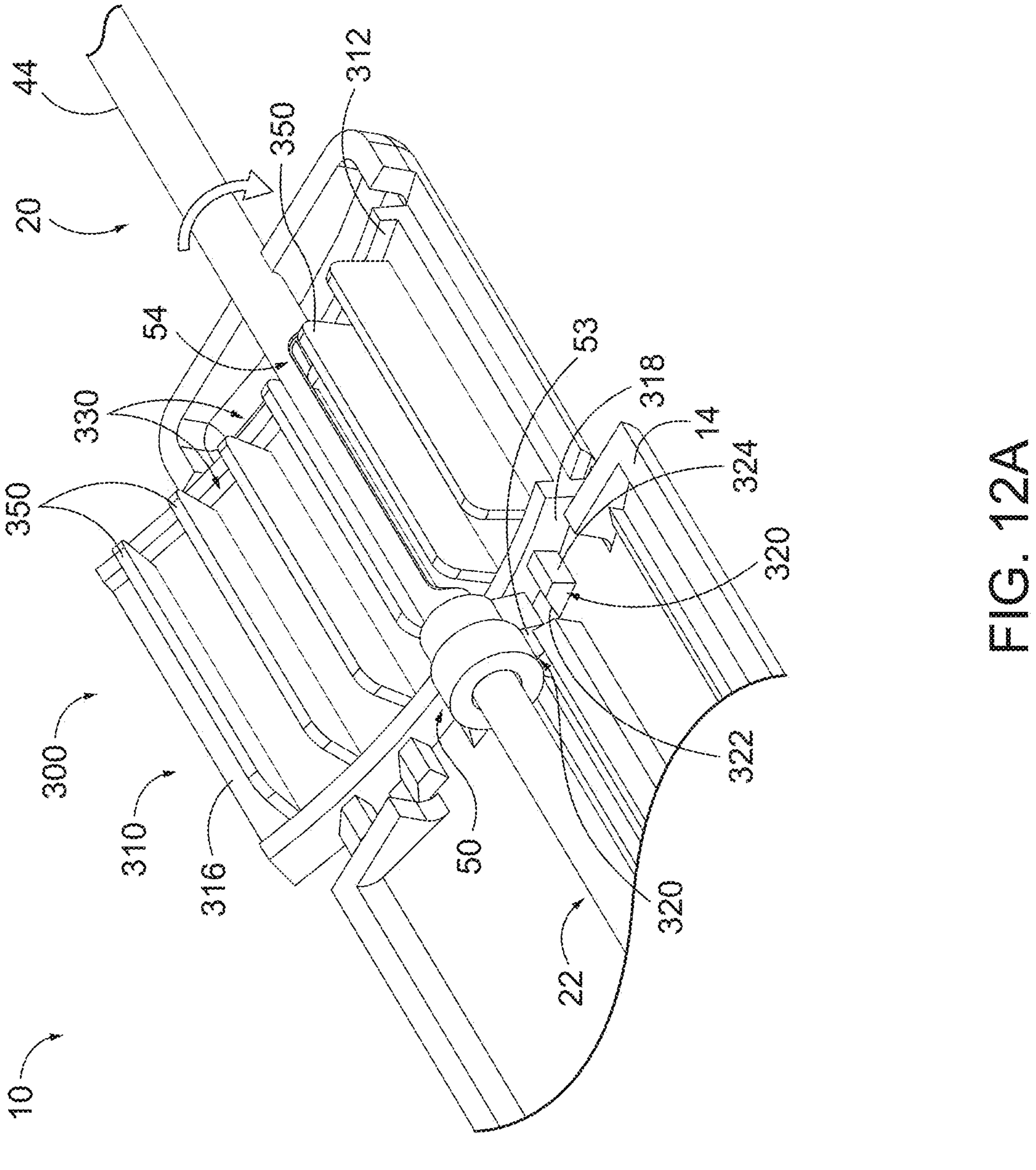
FIG. 12A depicts another perspective view of the tissue sample holder of FIG. 11, with the tissue sample holder positioned to collect a tissue sample.

FIG. 12A shows tissue sample holder (300) incorporated into biopsy device (10). As can be seen, tissue sample holder (300) can be received within a channel or other receiving features or components defined by outer housing (14) of biopsy device (10). Suitable channels within outer housing (14) can be shaped to generally correspond to the shape of base (310) such that base (310) can ride within the channel Additionally, suitable channels can be configured to receive base (310) just below needle assembly (20). In the preset example, the relationship between base (310) and needle assembly (20) is such that base (310) can freely translate transversely beneath needle assembly (20), while wipers (350) can still fully engage tissue collection feature (54). As will be described in greater detail below, this configuration permits base (310) to be movable to index a sample chamber (330) with needle assembly (20), while also permitting wipers (350) to engage tissue collection feature (54) to promote removal of tissue samples therefrom.

Figure 12B:
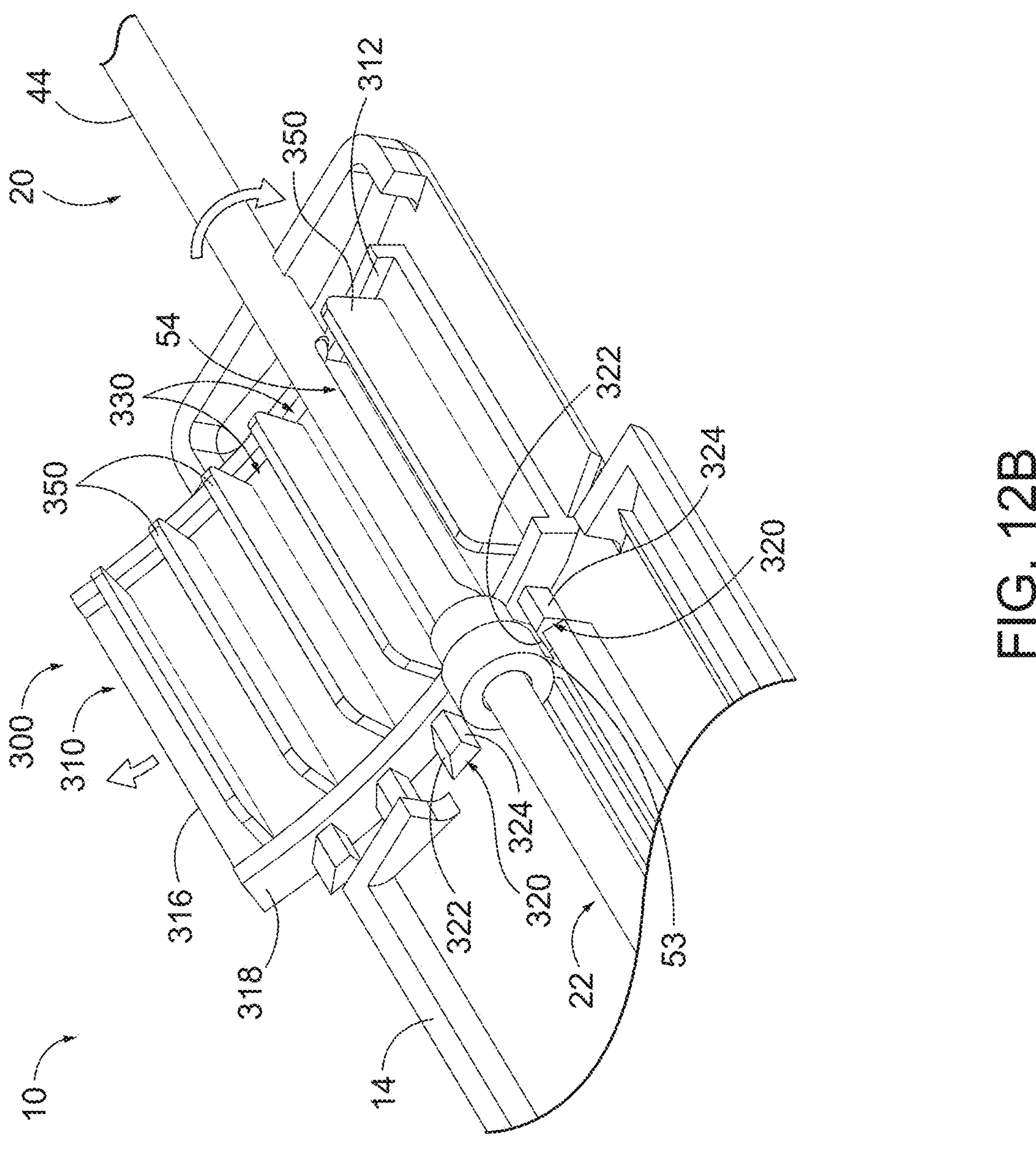
FIG. 12B depicts a still another perspective view of the tissue sample holder of FIG. 11, with the tissue sample holder translating to collect the tissue sample.
Figure 12C:
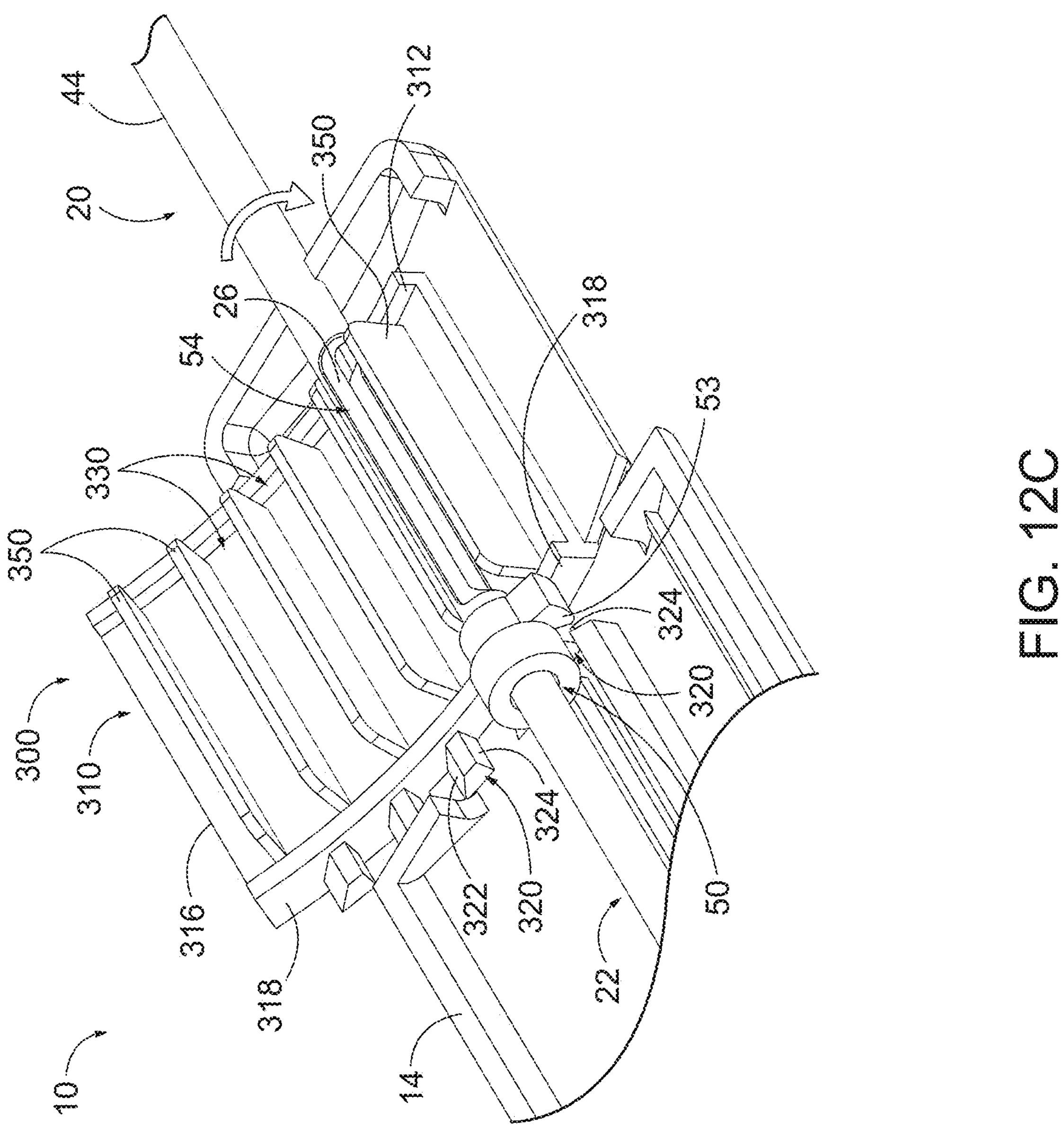
FIG. 12C depicts a yet another perspective view of the tissue sample holder of FIG. 11, with the tissue sample holder positioned to collect another tissue sample.

FIGS. 12A-12C show an exemplary use of tissue sample holder (300) to collect a severed tissue sample. Collection of a severed tissue sample begins in FIG. 12A. At the stage shown in FIG. 12A, it should be understood that cutter (40) and piercer (22) have already been actuated by drive assembly (100) to sever a tissue sample and transport the severed tissue sample proximally to tissue collection feature (54). Once a severed tissue sample has been transported proximally, cutter (40) and piercer (22) can be rotated as shown in FIG. 12A. This rotation results in tissue collection feature (54) rotating in a clockwise direction from an upward orientation to a downward orientation.

Rotation of cutter (40) and piercer (22) also results in rotation of driver (53) of end portion (50). In particular, driver (53) is generally aligned with tissue collection feature (54) such that driver (53) likewise moves from an upward orientation to a downward orientation. As driver (53) reaches the downward orientation, driver (53) sweeps between two manipulators (320) of tissue sample holder (300), which is permitted by angled surface (322) of a manipulator (320) positioned laterally relative to driver (53).

As driver (53) is rotated further towards the downward orientation, at least a portion of driver (53) engages a drive surface (324) of a given manipulator (320). Due to the orientation of drive surface (324), continued rotation of driver (53) results in the given manipulator (320) being pushed transversely by driver (53). As the given manipulator (320) is pushed transversely, base (310) is likewise pushed transversely.

Continued rotation of cutter (40) and piercer (22) results in translation of base (310) towards the position shown in FIG. 12B. As can be seen, this causes a given wiper (350) to translate transversely into tissue collection feature (54) and sweep across notch (26). As wiper (350) sweeps across notch (26), a severed tissue sample is displaced from tissue collection feature (54) and into a given sample chamber (330) of tissue sample holder (300). Thus, tissue collection in the present example is provided by translation of wiper (350) being coordinated with rotation of cutter (40) and piercer (22).

Further rotation of cutter (40) and piercer (22) can result in further translation of base (310) until driver (53) disengages from manipulator (320). As seen in FIG. 12C, this rotation can continue until driver (53) is rotated approximately 360 degrees from the original position shown in FIG. 12A to setup collection of another tissue sample using another manipulator (320). This pattern of rotation and tissue collection can be repeated in a sequence until all sample chambers (320) are filled. Alternatively, at any stage, base (310) can be manually actuated to disrupt the collection sequence and begin collecting samples at a previously indexed sample chamber (320) to place multiple tissue samples within each sample chamber.

Figure 13:
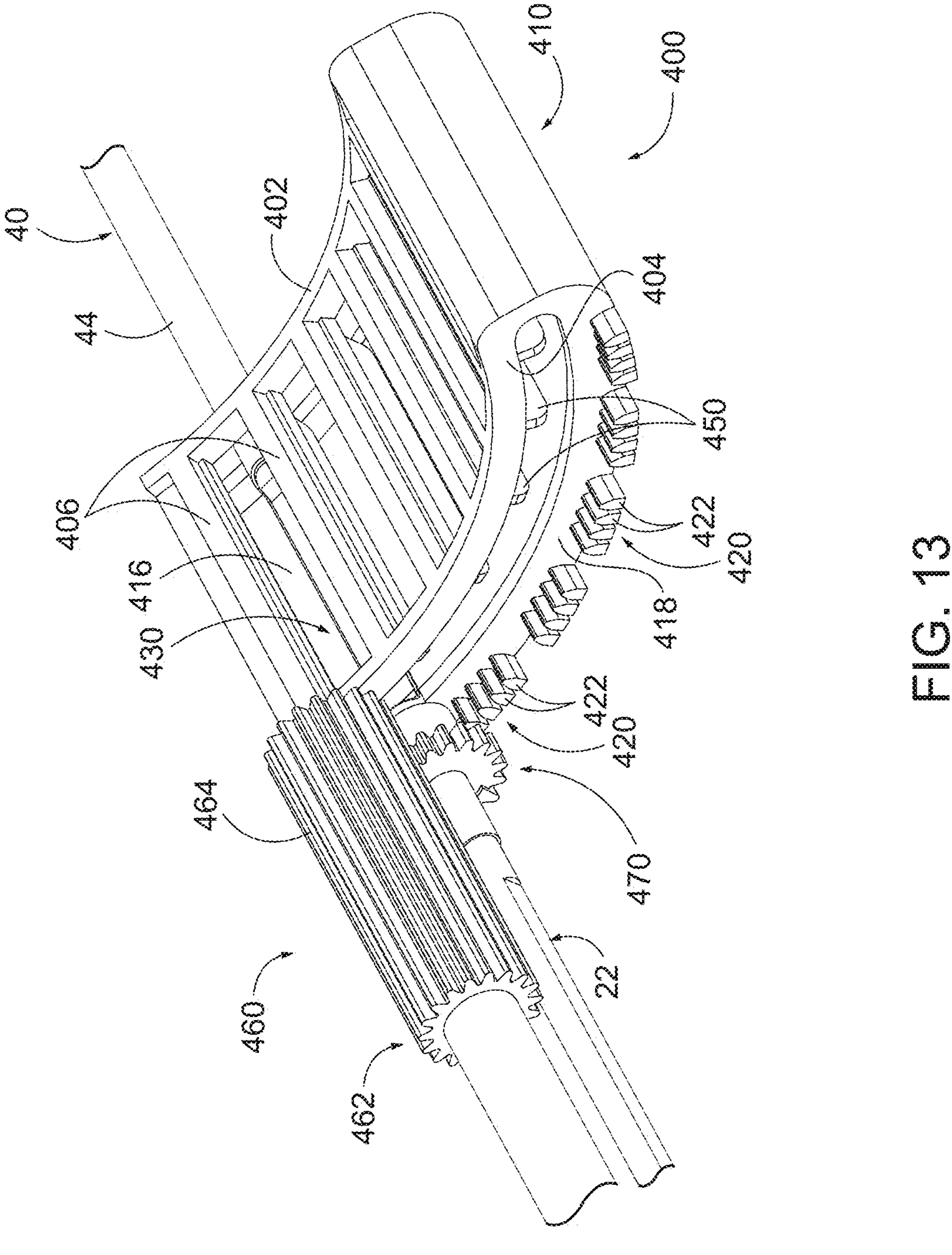
FIG. 13 depicts a perspective view of still another exemplary tissue sample holder that can be readily incorporated into the biopsy device of FIG. 1.

III. Exemplary Alternative Tissue Sample Holder with Translatable Upper Wipers FIG. 13 shows another exemplary tissue sample holder (400) that can be readily incorporated into biopsy device (10) described above. Tissue sample holder (400) of the presented example includes a base (410) having a plurality of wipers (450). As with tissue sample holder (200) described above, tissue sample holder (400) of the present example is generally configured to collect a plurality of tissue samples from tissue collection feature (54) of needle assembly (20) during a biopsy procedure. However, unlike tissue sample holder (200) described above, tissue sample holder (400) of the present example configured to be movable by a gear assembly (460) that is optionally in communication with needle assembly (20) to collect one or more tissue samples from tissue collection feature (54).

Figure 14:
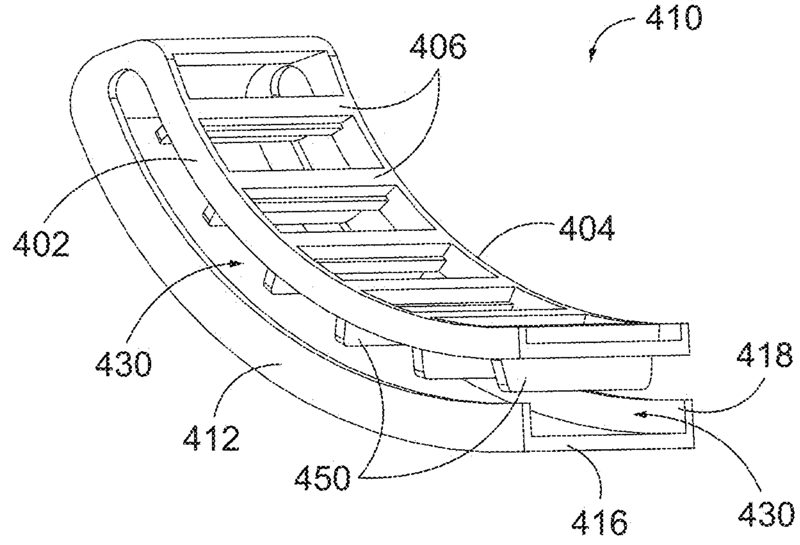
FIG. 14 depicts a perspective view of a base of the tissue sample holder of FIG. 13.
Figure 15:
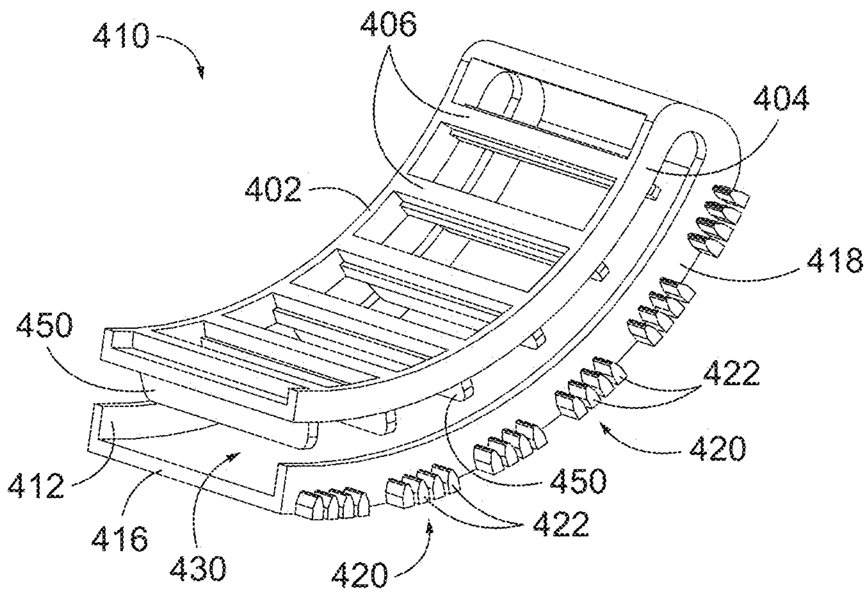
FIG. 15 depicts another perspective view of the base of FIG. 14.

Base (410) is best seen in FIGS. 14 and 15. As can be seen, base (410) generally defines an arcuate shape that defines at least some concavity. Although base (410) of the present example defines an arcuate shape, it should be understood that in other examples, base (410) can define a flat configuration. Base (410) includes a distal wall (412), a proximal wall (418), and a floor (416) extending between a portion of distal wall (412) and a portion of proximal wall (418). Both proximal wall (418) and distal wall (412) extend upwardly from floor (416). Proximal wall (418) and distal wall (412) further extend longitudinally along the entire length of floor (416). Accordingly, it should be understood that proximal wall (418) and distal wall (412) enclose the proximal end and distal end of floor (416), respectively. This enclosure defines a single sample chamber (430) within body (410).

Distal wall (412), floor (416) and proximal wall (418) are all shown in the present example as having a solid construction. However, it should be understood that in other examples, any of distal wall (412), floor (416), and/or proximal wall (418) can include one or more vents to provide ventilation. For instance, in some examples floor (416) can include a plurality of vent openings or vent slots to provide drainage of fluid during the collection of tissue samples. Suitable vent openings can be generally sized to permit the flow of liquid, while stopping the flow of solid substances such as tissue samples. One or more vents can likewise be disposed in distal wall (412) or proximal wall (418) to further promote drainage of liquid.

Base (410) further includes a distal upper wall (402) and a proximal upper wall (404) generally oriented above distal wall (412) and proximal wall (418). In particular, both distal upper wall (402) and proximal upper wall (404) extend from one side of distal wall (412) and proximal wall (418), respectively, before curving around approximately 180 degrees such that distal upper wall (402) and proximal upper wall (404) extend back over top of distal wall (412) and proximal wall (418). Distal upper wall (402) and proximal upper wall (404) are further spaced from distal wall (412) and proximal wall (418), respectively, by a distance approximately corresponding to the size of needle assembly (20). Thus, base (410) is generally configured to receive needle assembly (20) between distal upper wall (402) and distal wall (412) on the distal end and proximal upper wall (404) and proximal wall (418) on the proximal end.

Distal upper wall (402) and proximal upper wall (404) are interconnected by a plurality of slats (406). Slats (406) are generally configured to provide additional structural rigidity to base (410). Each slat (406) is generally sized to approximately correspond to the thickness of each wiper (450). As will be described in greater detail below, each slat (406) generally provides structural support for a corresponding wiper (450) to assist with collection of tissue samples.

Base (410) further includes a plurality of manipulators (420) extending from the proximal face of proximal wall (418). As will be described in greater detail below, each manipulator (420) is generally configured to engage a portion of gear assembly (460) to drive movement of base (410) during tissue collection and thereby index a given wiper (450) with tissue collection feature (54). Base (410) of the present example includes six manipulators (420), although any suitable number can be used. For instance, in the present example, each manipulator (420) corresponds to a particular wiper (450). Thus, in an example with additional wipers (450), additional manipulators (420) can likewise be used.

Each manipulator (420) includes a plurality of gear teeth (422) grouped together to form a single manipulator (420). As will be described in greater detail below, teeth (422) are generally configured to engage gear assembly (460) to permit manipulation of base (410). It should be understood that various alternative shapes for each manipulator (420) can be used. For instance, in the present example, the particular geometric shape of each manipulator (420) is generally configured to interact with specific structures of gear assembly (460). Thus, in other examples where a different drive mechanism may be used, different manipulator (420) geometries can be used. By way of example only, in some examples, manipulators (420) can be configured as teeth in a rack to engage a gear, pawls, cams, and/or etc.

Wipers (450) are arranged on base (410) and spaced in even intervals. Each wiper (450) extends downwardly from a corresponding slat (406) towards floor (416). Each wiper (450) also extends across the length of each corresponding slat (406) from distal upper wall (402) to proximal upper wall (404). In the present example, six wipers (450) are included. However, it should be understood that in other examples various alternative numbers of wipers (450).

Wipers (450) further extend downwardly into the space defined between distal wall (412) and upper distal wall (402), and proximal wall (418) and upper proximal wall (404), respectively. Thus, wipers (450) of the present example are configured to protrude into the interior of base (410). As will be described in greater detail below, this configuration can permit walls (402, 404, 412, 418) to ride along a portion of needle assembly (20), while wipers (450) can enter tissue collection feature (54) to extract tissue samples therefrom.

Unlike wipers (250) described above, wipers (450) of the present example have a generally continuous rectangular cross-section configuration with rounded corners. However, it should be understood that wipers (450) are still generally configured to engage with tissue collection feature (54) to remove tissue samples therefrom. Thus, it should be understood that wipers (450) are generally formed of a flexible yet partially resilient material such as rubber or elastomer. As similarly described above, wipers (450) are generally flexible enough to flex around features of needle assembly (20). This flexibility can be generally desirable to reduce trauma when each wiper (450) engages tissue, while also promoting complete engagement between each wiper (450) and tissue. Meanwhile, at least some resiliency is provided so that each wiper (450) can push or otherwise move a tissue sample. In some examples, the flexibility of each wiper (450) can be characterized in terms of a durometer. Although several suitable durometers can be used, one suitable durometer range is 30 to 80.

Figure 16:
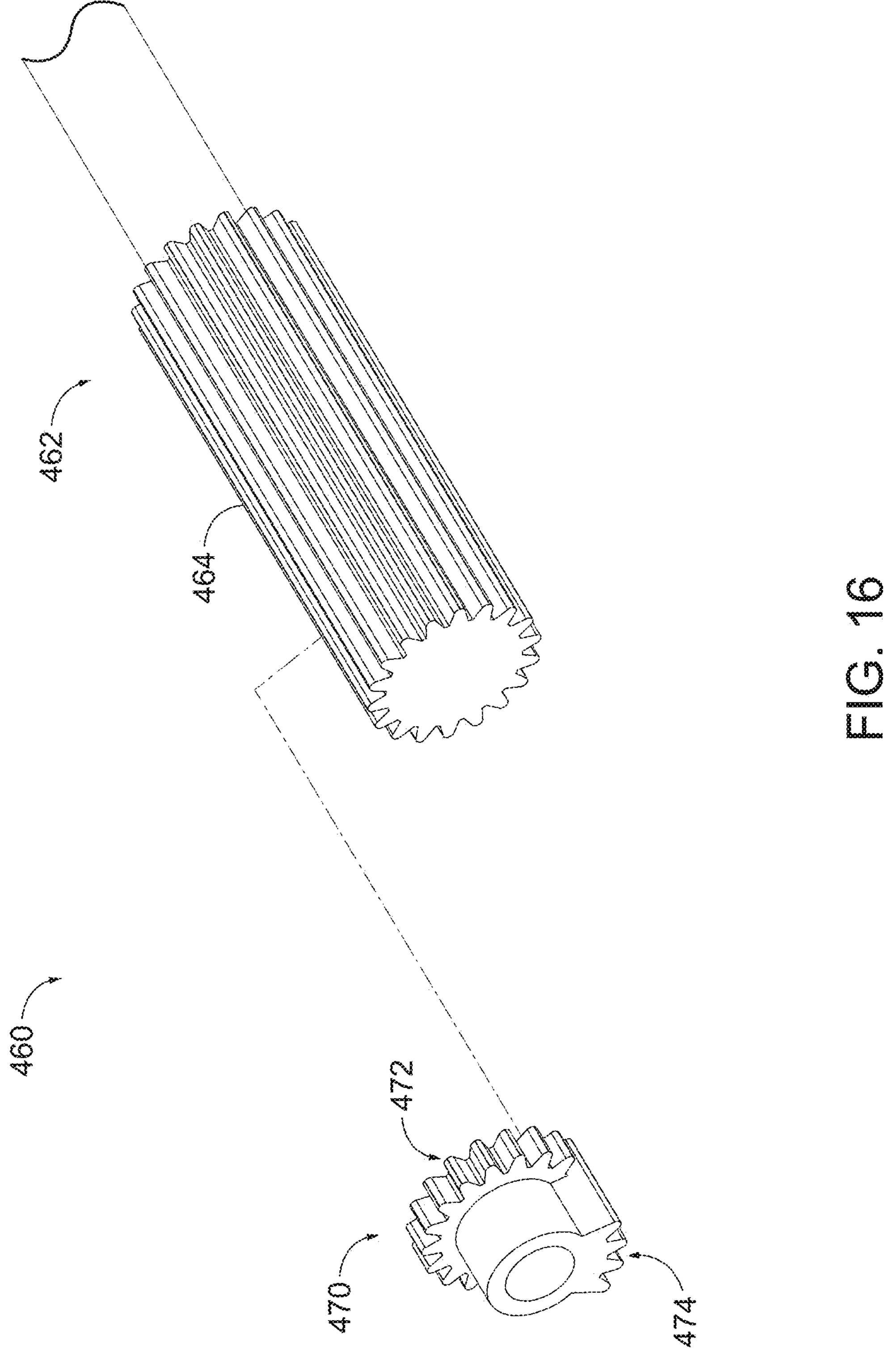
FIG. 16 depicts a perspective exploded view of a gear assembly of the tissue sample holder of FIG. 13.

FIG. 16 shows gear assembly (460) in greater detail. As can be seen, gear assembly (460) includes a drive shaft (462) having an elongate spur gear (464) and a partial intermittent gear (470). Shaft (462) is configured to be rotatably driven by a power source such as motor or a manually driven mechanism. In some examples, shaft (462) can be interconnected with drive assembly (100) such that rotation of shaft (462) is tied to operational features of drive assembly (100).

Elongate spur gear (464) is generally configured to drive rotation of partial intermittent gear (470). Elongate spur gear (464) has an elongated configuration to permit continuous drive of partial intermittent gear (470) during translation of partial intermittent gear (470) through a pre-determined range. In some examples, this can permit translation of needle assembly (20) by another mechanism (e.g., drive assembly (100)), while still permitting elongate spur gear (464) to rotate needle assembly (20).

Partial intermittent gear (470) includes a continuous portion (472) and an intermittent portion (474). Continuous portion (472) includes gear teeth oriented around the entire perimeter of partial intermittent gear (470). Meanwhile, intermittent portion (474) includes only four gear teeth isolated to a single section. In this configuration, continuous portion (472) is configured to mesh with elongate spur gear (464) such that partial intermittent gear (470) can be driven continuously in response to rotation of shaft (462). By contrast, intermittent portion (474) is configured to mesh with gear teeth (422) of each manipulator (420) to provide intermittent translation of base (410) even when partial intermittent gear (470) is continuously rotated. As will be described in greater detail below, this functionality can generally be used to influence the timing of translation of base (410) relative to the movement of other parts of biopsy device (10).

Figure 17A:
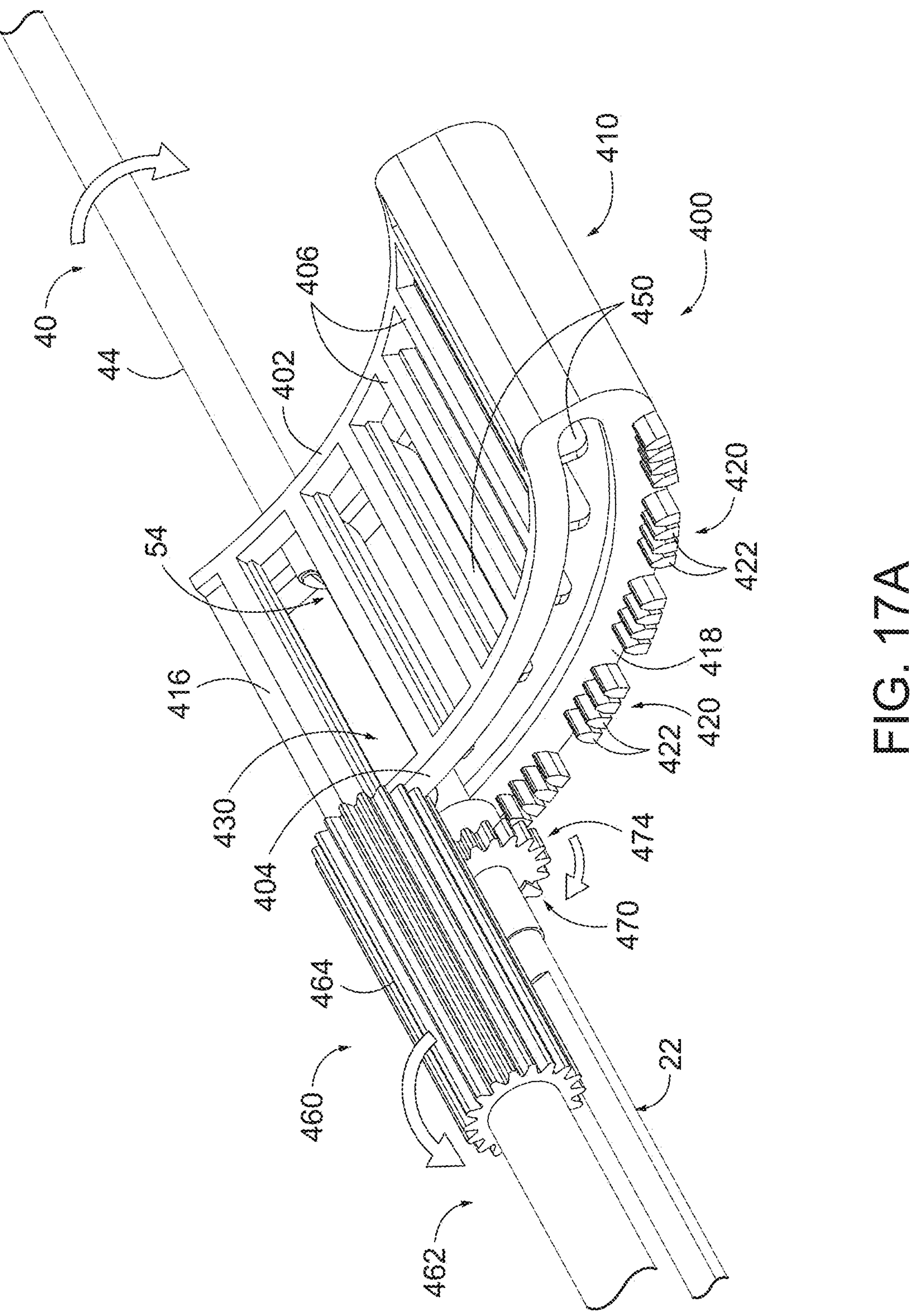
FIG. 17A depicts another perspective view of the tissue sample holder of FIG. 13, with the tissue sample holder positioned to collect a tissue sample.

FIGS. 17A-18C show an exemplary use of tissue sample holder (400) to collect a severed tissue sample. Collection of a severed tissue sample begins in FIGS. 17A and 18A. At the stage shown in FIGS. 17A and 18A, it should be understood that cutter (40) and piercer (22) have already been actuated by drive assembly (100) to sever a tissue sample and transport the severed tissue sample proximally to tissue collection feature (54). Once a severed tissue sample has been transported proximally, cutter (40) and piercer (22) can be rotated as shown in FIG. 17A. This rotation results in tissue collection feature (54) rotating in a clockwise direction from an approximate 10 o'clock position to an approximate 12 o'clock position.

Rotation of cutter (40) and piercer (22) is coordinated with rotation of drive shaft (462) of gear assembly (460). Alternatively, in some examples, rotation of cutter (40) and piercer (22) is provided by a separate drive mechanism similar to drive assembly (100) described above. In the present example, cutter (40) is rotated by continuous portion (472) of partial intermittent gear (470), which is rotated by elongate spur gear (474) of drive shaft (462). As seen in FIG. 17A, this rotation of partial intermittent gear (470) also causes translation of base (410) via engagement between intermittent portion (474) and gear teeth (422) of a given manipulator (420).

Figure 18A:
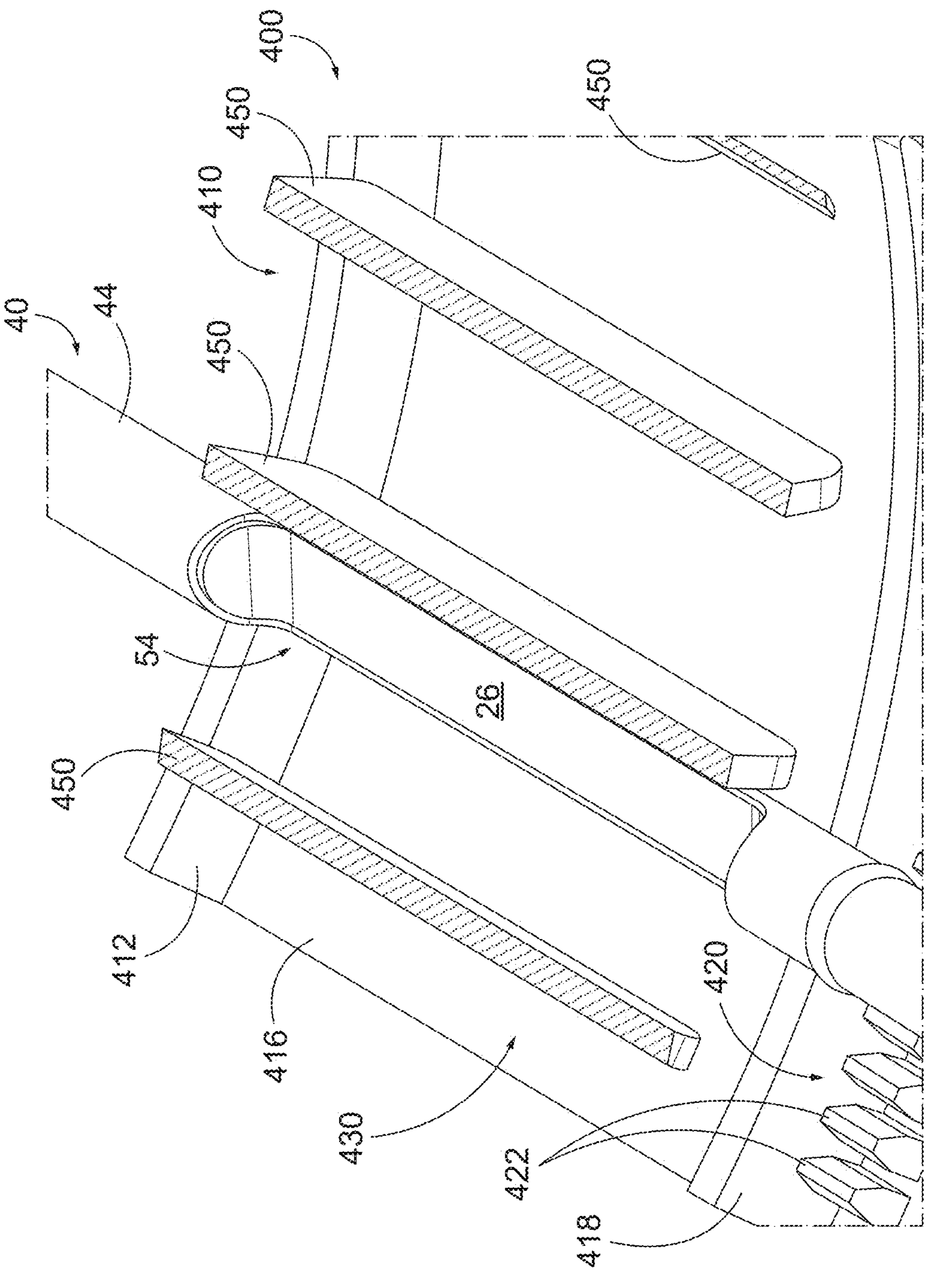
FIG. 18A depicts a partial perspective cross-sectional view of the tissue sample holder of FIG. 13, with a wiper of the tissue sample holder positioned to collect the tissue sample.
Figure 18B:
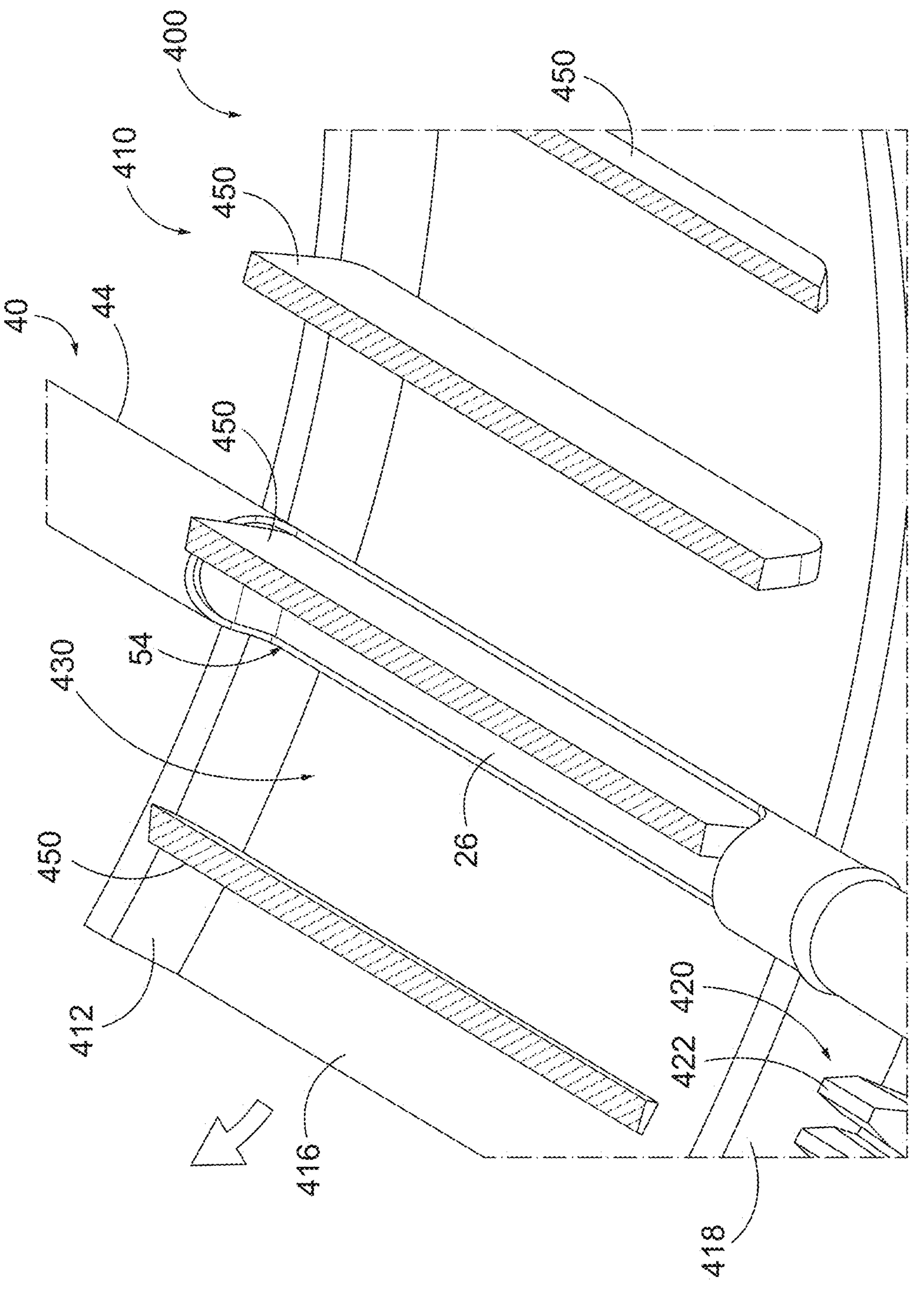
FIG. 18B depicts another partial perspective cross-sectional view of the tissue sample holder of FIG. 13, with the wiper of FIG. 18A sweeping across a notch of the piercer of the needle assembly of FIG. 2.

As cutter (40) and piercer (22) are rotated while base (410) is translated, a given wiper (450) is translated transversely into tissue collection feature (54). As shown in FIG. 18B, this transverse translation results in the given wiper (450) sweeping across notch (26). As wiper (450) sweeps across notch (26), a severed tissue sample is displaced from tissue collection feature (54).

After the severed tissue sample is displaced from tissue collection feature (54), the force of gravity can pull the severed tissue sample downwardly into sample chamber (430). Alternatively, in some uses surface tension in moisture may cause the severed tissue sample to remain on the given wiper (450) either temporarily until the force of gravity is sufficient, or until it is removed by an operator. Thus, tissue collection in the present example is provided by translation of wiper (450) being coordinated with rotation of cutter (40) and piercer (22).

Figure 17B:
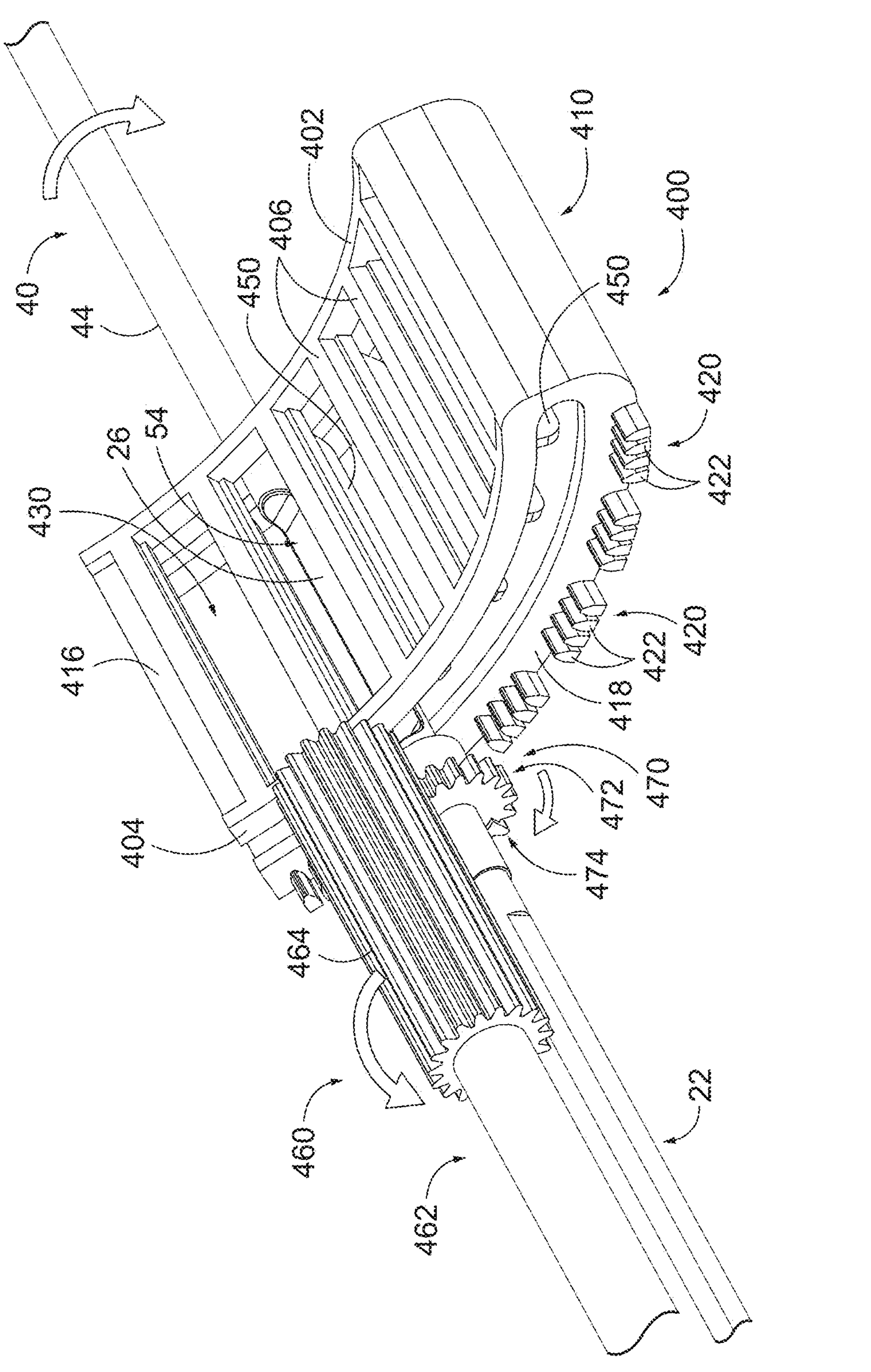
FIG. 17B depicts still another perspective view of the tissue sample holder of FIG. 13, with the tissue sample holder being translated to collect the tissue sample.
Figure 18C:
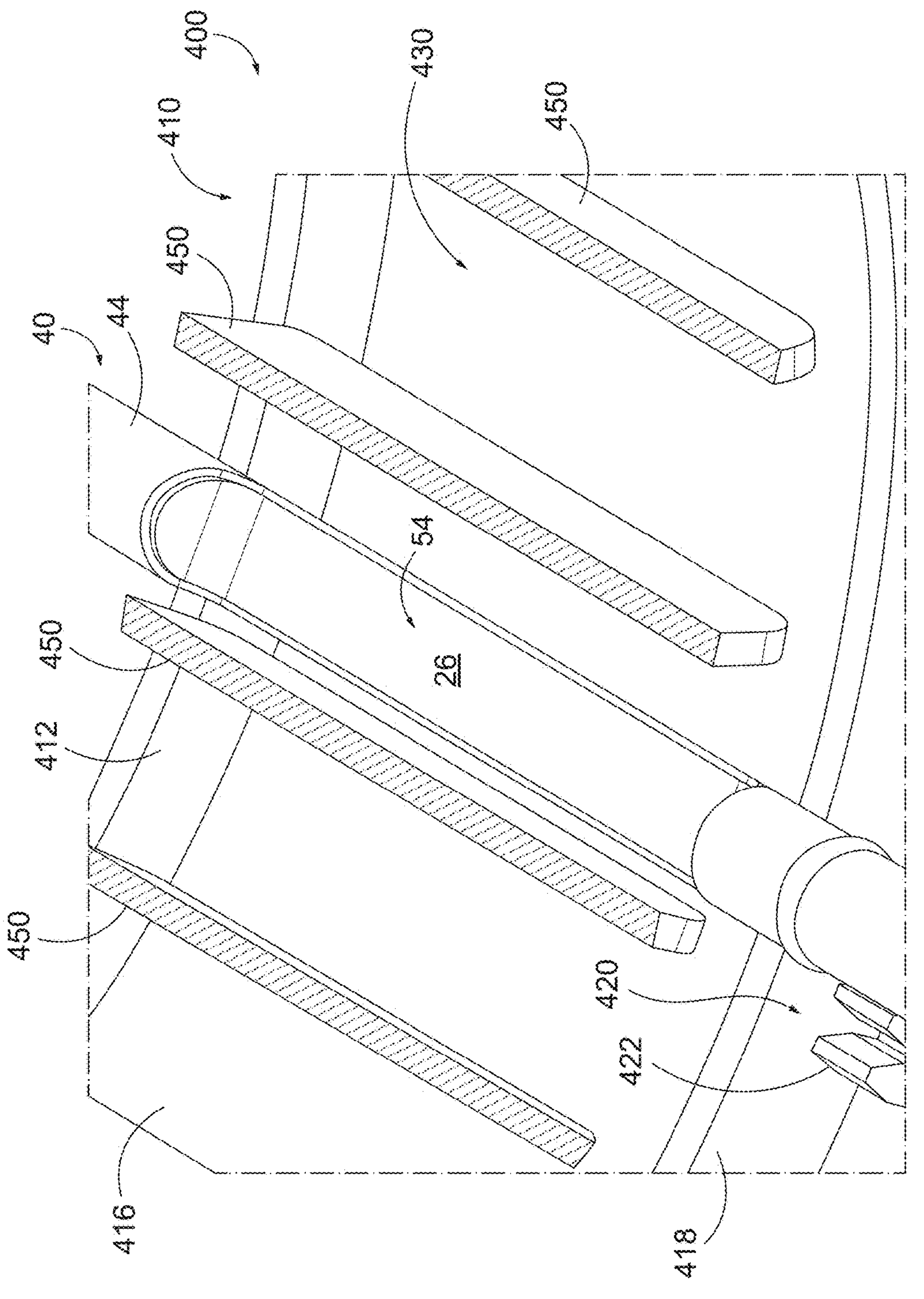
FIG. 18C depicts still another partial perspective cross-sectional view of the tissue sample holder of FIG. 13, with another wiper of the tissue sample holder positioned to collect another tissue sample.

Further rotation of cutter (40) and piercer (22) can result in further translation of base (410) until the given wiper (450) disengages from tissue collection feature (54), as shown in FIGS. 17B and 18C. At this stage, intermittent portion (474) of partial intermittent gear (470) can disengage from the given manipulator (420) associated with the given wiper (450). Once disengaged, partial intermittent gear (470) can continue to rotate cutter (40) and/or piercer (22), while base (410) remains stationary.

Rotation of cutter (40) and/or piercer (22) can thus continue until an approximately 360-degree rotation has been completed, returning cutter (40) and/or piercer (22) to the position shown in FIG. 17A. Another tissue sample can then be severed, and the process described above can be repeated with another manipulator (420) being engaged by intermittent portion (474) of partial intermittent gear (470). This pattern of rotation and tissue collection can be repeated in a sequence until all wipers (450) have been used. Alternatively, at any stage, base (410) can be manually actuated to disrupt the collection sequence and begin collecting samples at a previously indexed wiper (450) to collect multiple tissue samples with each wiper.

As described above, in some examples, rotation of cutter (40) and piercer (22) is provided by a separate drive mechanism similar to drive assembly (100) described above. It should be understood that in such examples, rotation of cutter (40) and/or piercer (22) can be independent from translation of base (410). For instance, in such examples cutter (40) and piercer (22) can be positioned to align with a given wiper (450) prior to any rotation of drive shaft (462) and thus translation of base (410) via partial intermittent gear (470). Once cutter (40) and/or piercer (22) are positioned as desired, drive shaft (462) can then begin to rotate to translate base (410) as similarly described above using partial intermittent gear (470). Thus, in some examples, cutter (40) and piercer (22) define a discrete series of movements relative to base (410) rather than such movements being coordinated with base (410). Such a configuration can be desirable to reduce additional complexity that may be required for coordinated motion.

IV. Exemplary Alternative Tissue Sample Holder with Rotatable Wiper

Figure 19:
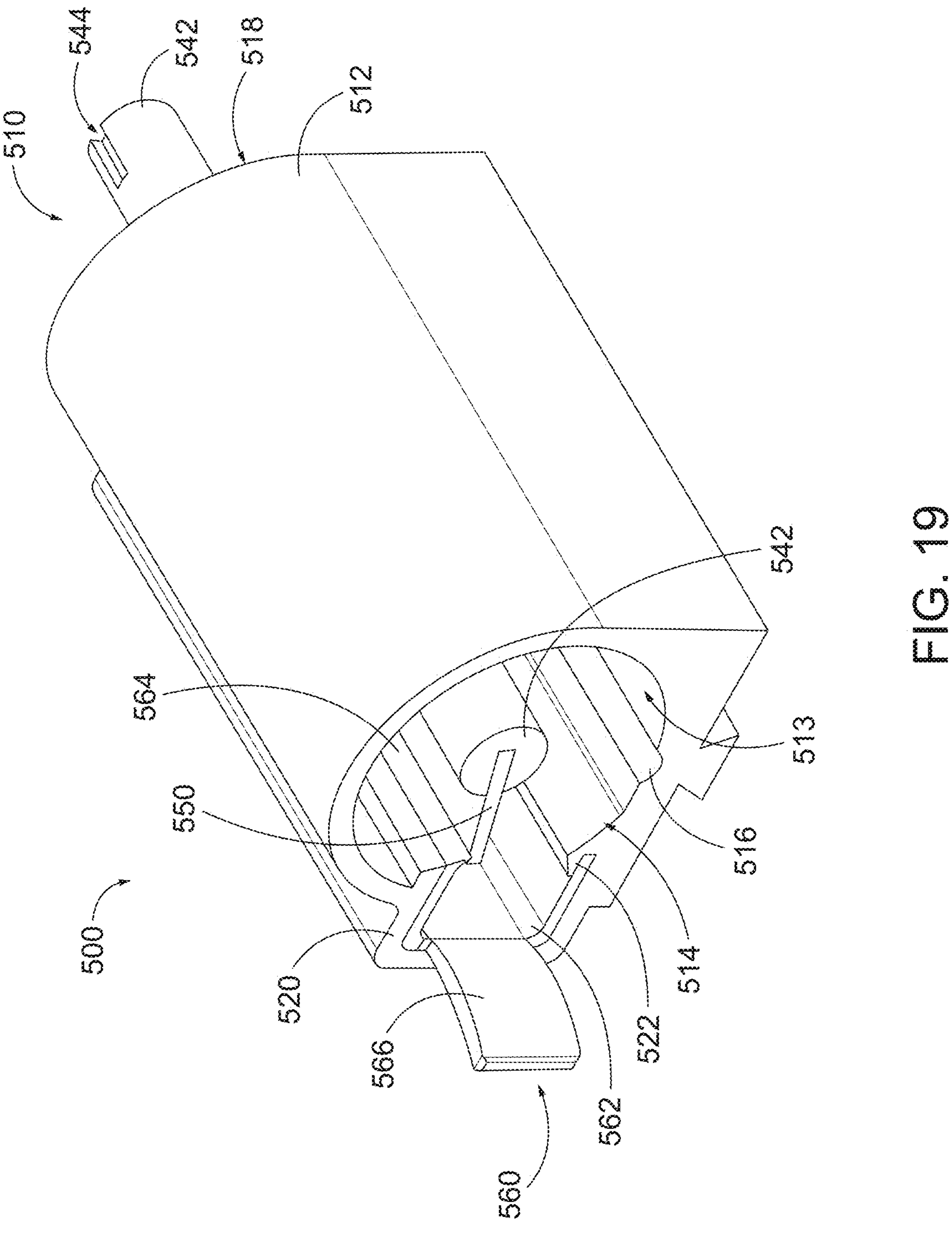
FIG. 19 depicts a perspective view of yet another exemplary tissue sample holder that can be readily incorporated into the biopsy device of FIG. 1.
Figure 20:
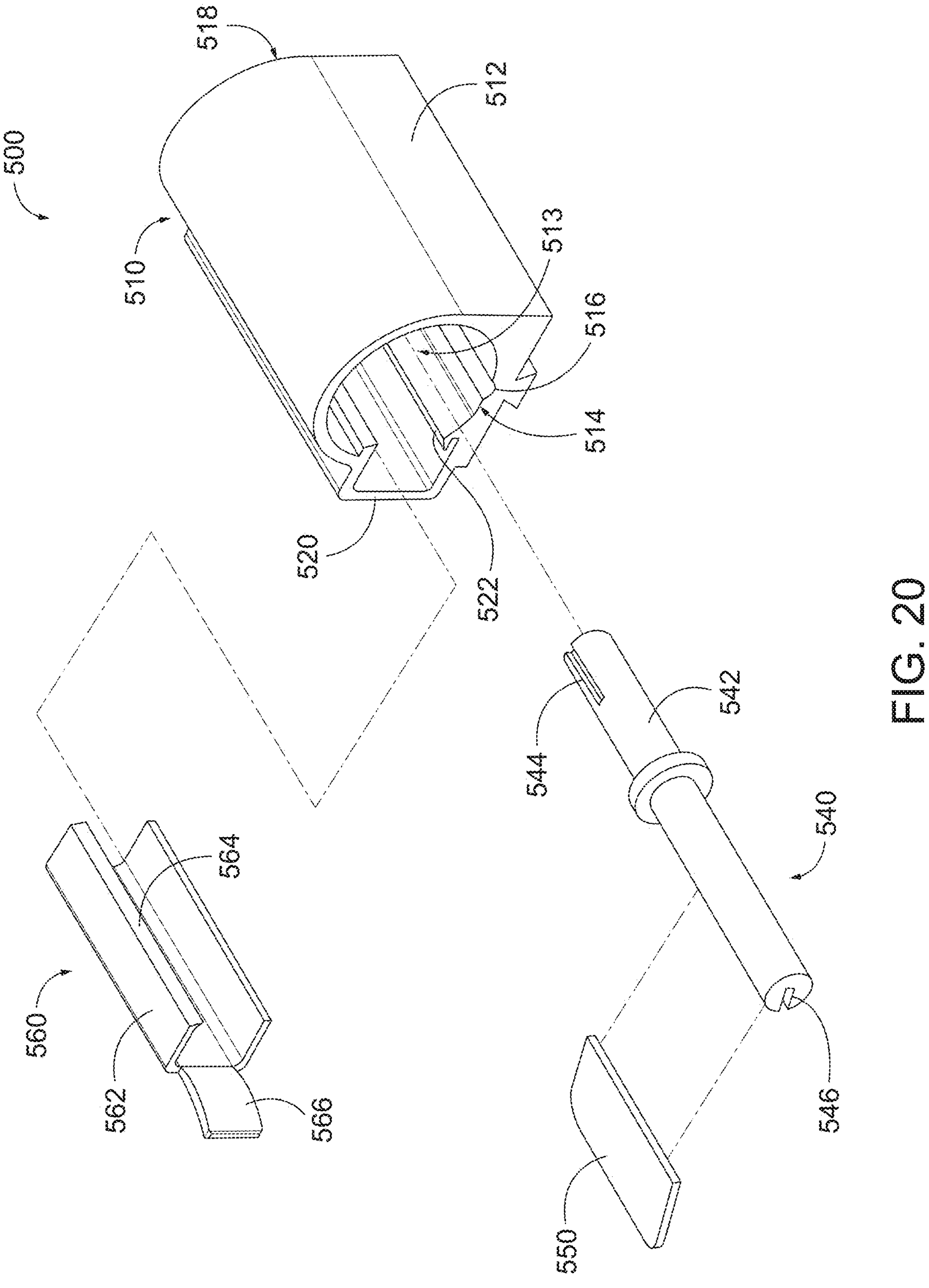
FIG. 20 depicts a perspective exploded view of the tissue sample holder of FIG. 19.

FIGS. 19 and 20 show another exemplary tissue sample holder (500) that can be readily incorporated into biopsy device (10) described above. Tissue sample holder (500) of the present example includes an extraction mechanism (540) disposed within a generally cylindrical outer housing (510). Tissue sample holder (500) is generally configured to collect a plurality of tissue samples from tissue collection feature (54) of needle assembly (20) during a biopsy procedure using rotation of extraction mechanism (540). As will be described in greater detail below, tissue sample holder (500) is generally configured to collect and store tissue samples in a bulk collection configuration of any suitable number.

Outer housing (510) includes a cylindrical body (512) defining a sample chamber (513) and an open distal end (514), a closed proximal end (518), and a needle receiving portion (516) extending between the open distal end (514) and the closed proximal end (518). In the present example, outer housing (510) is generally transparent to promote visibility of tissue samples during sample collection. Although outer housing (510) of the present example is shown as having open distal end (514), it should be understood that in other examples, open distal end (514) can be closed or capped to seal sample chamber (513) of outer housing (510) relative to the environment.

Needle receiving portion (516) is generally configured as a semi-cylindrical indentation or bulge in the otherwise cylindrical shape of outer housing (510). Needle receiving portion (516) is generally sized to correspond to the size and shape of needle assembly (20). Thus, needle receiving portion (516) generally defines a pocket or recessed area where needle assembly (20) can rest. As will be described in greater detail below, the particular depth of needle receiving portion (516) can have some relationship to the particular geometric configuration of tissue collection feature (54) of needle assembly (20) to assist with the extraction of a tissue sample from tissue collection feature (54).

Although not shown, it should be understood that closed proximal end (518) of outer housing (510) can include a shaft bore (not shown) and a needle bore (not shown). As will be described in greater detail below, a suitable shaft bore can be configured to receive a rotatable component of extraction mechanism (540) to permit rotation of extraction mechanism (540) relative to outside outer housing (510). A suitable needle bore can be sized to permit needle assembly (20) to pass proximally though closed proximal end (518). Although not shown, it should be understood that either the shaft bore and/or the needle bore can include seals, O-rings, gaskets, and/or etc. to seal sample chamber (513) of outer housing (510) relative to the environment.

Outer housing (510) further defines a tray receiver (520) adjacent to sample chamber (513). As will be described in greater detail below, tray receiver (520) is configured to receive a tissue tray (560) for the purpose of collecting tissue samples. In the present example, tray receiver (520) is formed as a generally rectangular channel. Tray receiver (520) can also be characterized has having a C-shaped cross-section due to one side of tray receiver (520) being open to sample chamber (513). Thus, tray receiver (520) is generally in communication with sample chamber (513) to permit tissue samples to be deposited within tissue tray (560).

Tray receiver (520) includes a locator (522) to promote holding tissue tray (560) in a predetermined position. In the present example, locator (522) is formed as a slight overhang, L-shaped portion, or J-shaped portion. As will be understood, this particular shape together with the rectangular shape of tray receiver (520) can help to maintain the position of tissue tray (560) within tray receiver (520).

Although tray receiver (520) of the present example is shown as having a particular shape, it should be understood that a variety of shapes can be used. For instance, as will be described in greater detail below, tray receiver (520) is generally complementary to the shape of tissue tray (560). Thus, in examples where the shape of tissue tray (560) is varied, the shape of tray receiver (520) can likewise be varied to complement tissue tray (560).

FIG. 20 shows extraction mechanism (540) in greater detail. As can be seen, extraction mechanism (540) includes a shaft (542) and a single wiper (550) projecting outwardly from shaft (542). Shaft (542) is generally rotatable to thereby rotate wiper (550) within outer housing (510) to collect and store tissue samples as each tissue sample is collected by needle assembly (20). The proximal end of shaft (542) includes a keyed portion (544) that is configured to communicate with either a manual or motorized driver to rotate shaft (542). Although keyed portion (544) of the present example is formed of a generally rectangular channel or keyway, it should be understood that keyed portion (544) can have a variety of configurations suitable to transfer rotary motion such as keys, a plurality of keyways or channels, a square shape, a hexagonal shape, a D-shape, and/or etc.

Although not shown, it should be understood that shaft (542) can be driven using keyed portion (544) by a variety of mechanisms. For instance, in some examples, keyed portion (544) is rotatably coupled to any suitable portion of drive assembly (100) such as cutter drive assembly (120), piercer drive assembly (130), firing assembly (140), or some combination thereof. Such a configuration may be desirable to coordinate rotation of shaft (542) with movement of cutter (40) and/or piercer (22). Alternatively, biopsy device (10) can be configured to include an entirely separate drive mechanism for shaft (542). For instance, in some examples, an independent motor can be used to directly power rotation of shaft (542) via a transmission or other drive mechanism. In still other examples, rotation of shaft (542) can be driven by a manual rotation mechanism such as a thumbwheel, pushbutton, or other similar mechanism.

The distal end of shaft (542) includes a coupler channel (546) extending inwardly from an exterior surface of shaft (542). Coupler channel (546) is generally configured to receive wiper (550) to provide a secure base for wiper (550) to fasten to. Coupler channel (546) of the present example is formed of a generally rectangular channel. In other examples, various alternative shapes can be used such as triangular, circular, square, or the like. In addition, or in the alternative, in some examples coupler channel (546) can be configured as a protrusion to engage a corresponding channel within wiper (550). Although not shown, it should be understood that coupler channel (546) can extend axially along the length of shaft (542) for a length approximately equivalent to the length of wiper (550).

Wiper (550) of the present example is generally configured as a thin rectangular strip with rounded outer corners.

As described above, wiper (550) is configured for receipt within coupler channel (546) of shaft (542). Suitable coupling between wiper (550) can shaft (542) can be through a variety of means such as adhesion bonding, welding, mechanical fastening, and/or etc. Although the present example is shown as only including a single wiper (550), it should be understood that in other examples a plurality of wipers (550) can be included oriented around shaft (542) similarly to the orientation of wipers (250) described above.

Wiper (550) extends outwardly relative to coupler (546) away from shaft (542). When extraction mechanism (540) is disposed within outer housing (510), the axial extension of wiper (550) is such that the outer edge of wiper (550) contacts the inner surface of outer housing (510). Accordingly, it should be understood that wiper (550) is generally configured to slide along the inner surface of outer housing (510) to sweep one or more tissue samples around inner surface of outer housing (510).

Wiper (550) is generally formed of a flexible yet partially resilient material such as rubber or elastomer. For instance, wiper (550) is generally flexible enough to flex around the interface between outer housing (510) and needle assembly (20). This flexibility can be generally desirable to reduce trauma when wiper (550) engages tissue, while also promoting complete engagement between wiper (550) and tissue. Meanwhile, at least some resiliency is provided so that wiper (550) can push or otherwise move a tissue sample. In some examples, the flexibility of wiper (550) can be characterized in terms of a durometer. Although several suitable durometers can be used, one suitable durometer range is 30 to 80.

As described above, tissue sample holder (500) further includes tissue tray (560), which is configured to be received within tray receiver (520) of outer housing (510). Tissue tray (560) includes a tissue receiver (562) configured to receive a plurality of tissue samples and a handle (566) extending proximally from the tissue receiver (562). Tissue receiver (562) has a generally C-shaped cross-section that extends for an axial length approximately corresponding to the length of wiper (550). An upper portion of tissue receiver (562) includes a collection tooth (564) protruding outwardly and downwardly relative to the upper surface of tissue receiver (562). As will be described in greater detail below, collection tooth (564) is generally configured to remove a tissue sample from the surface wiper (550).

Tissue receiver (562) of the present example generally comprises a solid construction. However, it should be understood that in other examples, tissue receiver (562) can include one or more vents to assist with fluid management. For instance, in some examples the bottom surface of tissue receiver (562) can include one or more vent openings, slots, perforations, and or etc., to assist with drainage of various fluid encountered during a biopsy procedure. As such, it should be understood that various vents can be configured to promote the flow of liquid, while also preventing the flow of larger solid matter such as tissue samples.

Handle (566) extends proximally from tissue receiver (562). Handle (566) of the present example comprises thin rectangular strip. Handle (566) is generally configured for gripping by an operator for removal or insertion of tissue tray (560) relative to outer housing (510). The shape of handle (566) is generally curved to promote gripping. In addition, or in the alternative, handle (566) can also be equipped with various grip features such as bulges, protrusions, perforations, and/or etc. to promote gripping.

Figure 21A:
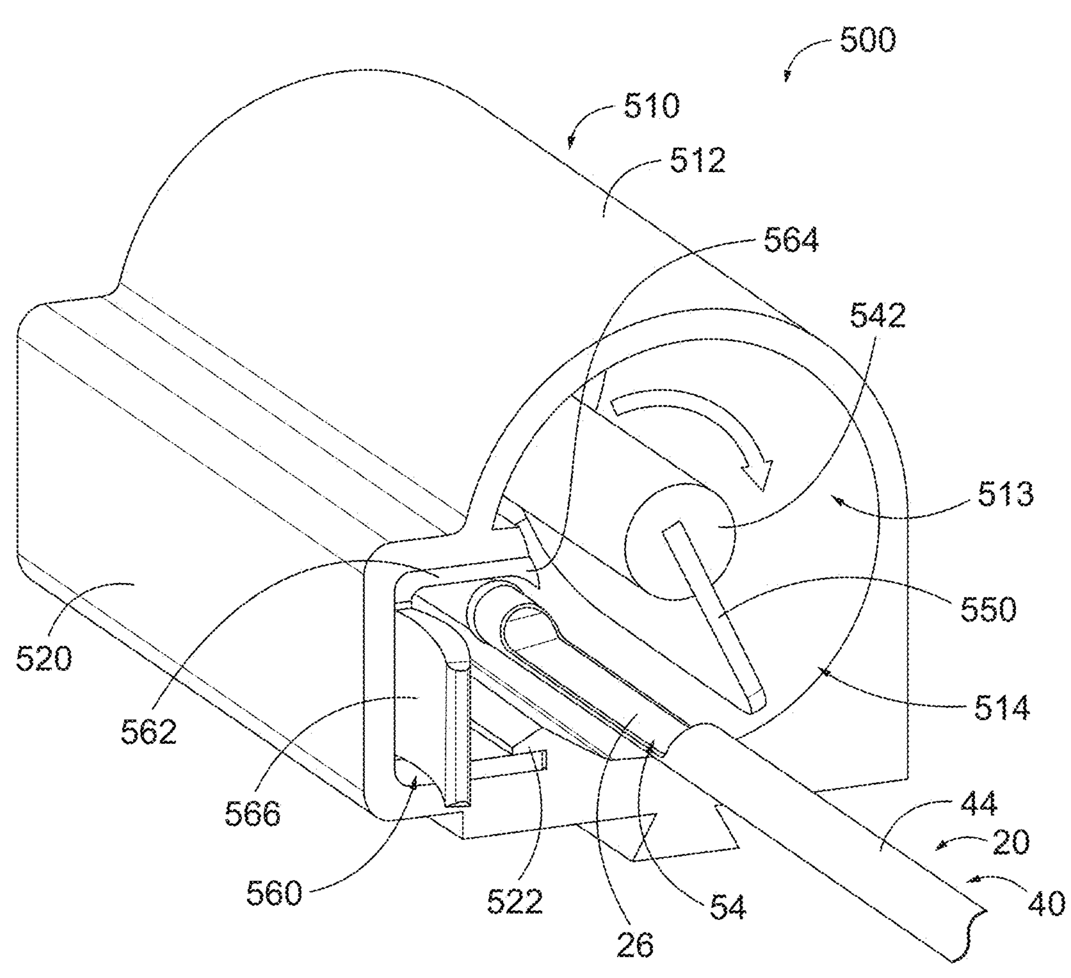
FIG. 21A depicts another perspective view of the tissue sample holder of FIG. 19, with a wiper of the tissue sample holder positioned to collect a tissue sample.
Figure 21B:
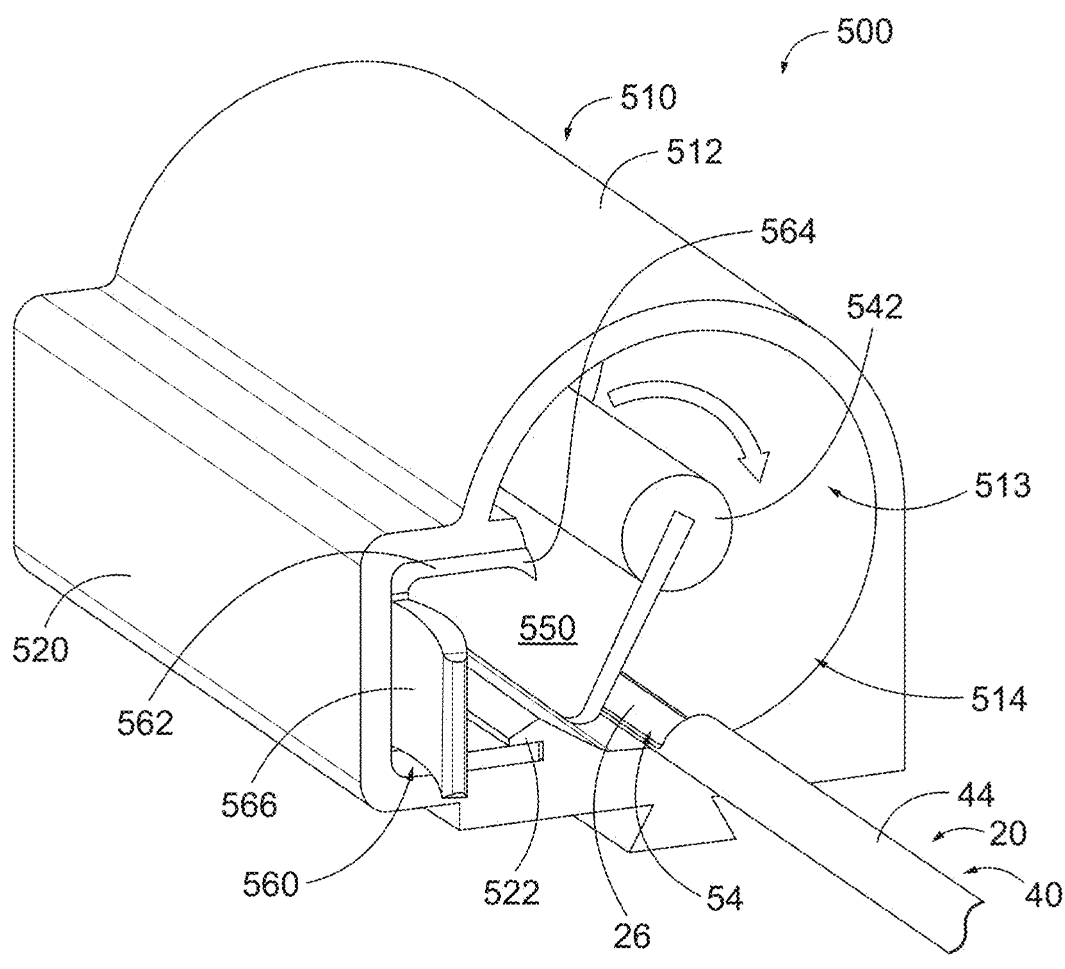
FIG. 21B depicts still another perspective view of the tissue sample holder of FIG. 19, with the wiper of FIG. 21A being rotated to move the tissue sample.
Figure 21C:
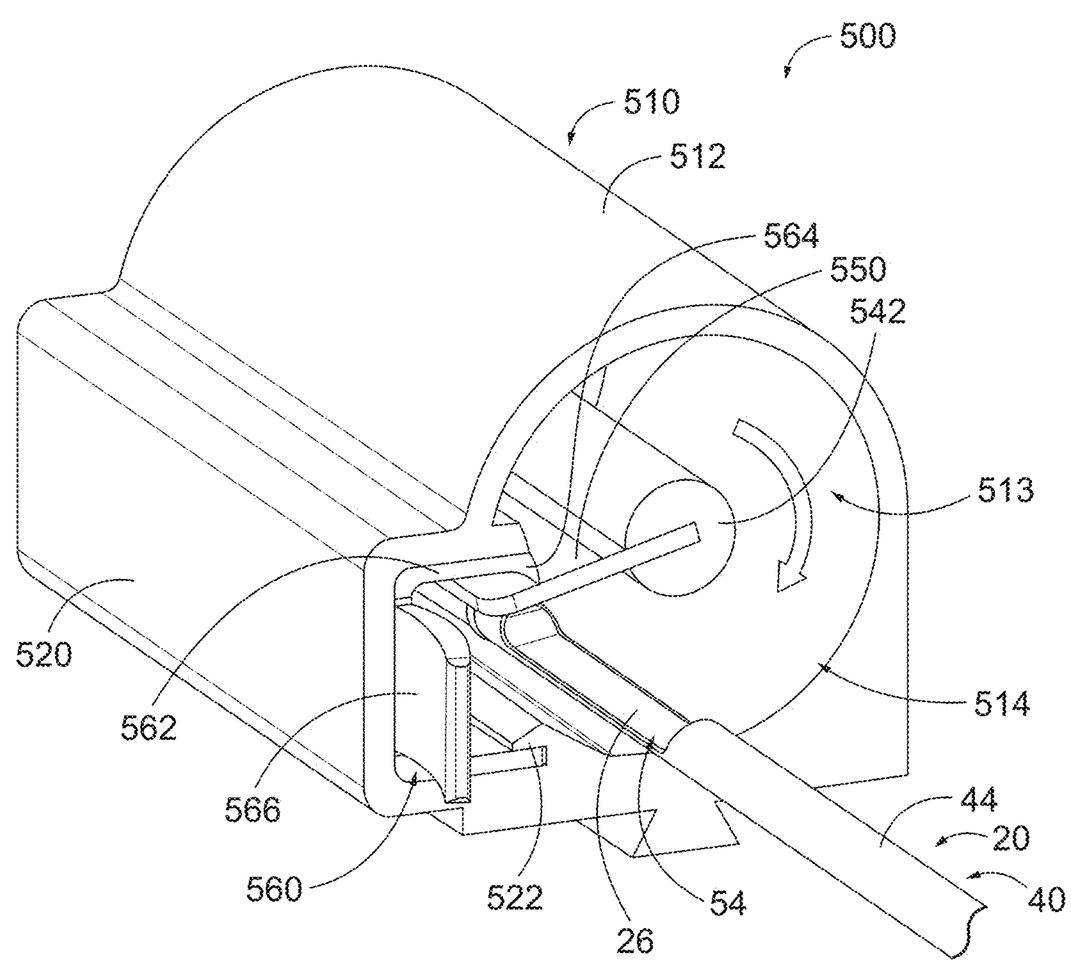
FIG. 21C depicts yet another perspective view of the tissue sample holder of FIG. 19, with the wiper of FIG. 21A being rotated to deposit the tissue sample within a tissue tray.

FIGS. 21A and 21C show an exemplary use of tissue sample holder (500) to collect a tissue sample from needle assembly (20). As can be best seen in FIG. 21A, collection of a tissue sample using tissue sample holder (500) can begin after cutter (40) and piercer (22) have been driven by drive assembly (100) to sever and collect a tissue sample. In particular, once the tissue sample has been severed, the tissue sample is transported to tissue collection feature (54) using notch (26) of piercer (22).

In the present example, tissue sample holder (500) is positioned along the axis of needle assembly (20) such that wiper (550) is aligned with tissue collection feature (54). Accordingly, to collect the tissue sample, shaft (542) can be rotated to rotate wiper (550) within sample chamber (513) to sweep wiper (550) adjacent to tissue collection feature (54) as shown in FIG. 21A. Further rotation of shaft (542) can cause wiper (550) to sweep across notch (26). As wiper (550) sweeps across notch (26), wiper (550) engages the tissue sample to push the tissue sample out of tissue collection feature (54) to the position shown in FIG. 21B.

Once wiper (550) sweeps across notch (26), rotation of shaft (542) can continue as shown in FIG. 21B. Continued rotation results in the tissue sample being moved around the interior of outer housing (210) to permit the tissue sample to be moved towards tissue tray (560). As shown in FIG. 21C, the tissue sample can be deposited in tissue tray (560) by wiper (550) sweeping across collection tooth (564) of tissue tray (560). This motion can cause the severed tissue sample to be wiped off of wiper (550) and onto collection tooth (564). The force of gravity can then cause the severed tissue sample to fall into tissue receiver (562) for storage.

Once the severed tissue sample is collected within tissue tray (560), rotation of shaft (542) can continue in coordination with sequential movement of cutter (40) and piercer (22) for the severing and collection of another tissue sample. Alternatively, rotation of shaft (542) can temporarily cease to permit cutter (40) and piercer (22) to reposition and collect another tissue sample. Regardless, once another tissue sample is collected, rotation of shaft (542) can be used to again sweep wiper (550) across notch (26) to collect another tissue sample. The same process can then be repeated any suitable number of times until tissue tray (560) is full or a desired number of tissue samples have been collected.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A core needle biopsy device, comprising: a needle assembly, wherein the needle assembly includes a piercer and a hollow cutter, wherein the piercer includes a sharp distal tip and a notch proximal to the distal tip, wherein the piercer is slidably disposed within the cutter to sever a tissue sample into the notch of the piercer; a drive assembly configured to selectively move the piercer and the cutter; and a tissue sample holder having a sample chamber and a wiper, wherein the wiper is movable relative to the piercer and cutter to manipulate a severed tissue sample into the sample chamber.

Example 2

The core needle biopsy device of Example 1, wherein the tissue sample holder includes a rotatable shaft, wherein the wiper is secured to the shaft such that rotation of the shaft is configured to rotate the wiper relative to the piercer to thereby manipulate a severed tissue sample into the sample chamber.

Example 3

The core needle biopsy device of Example 2, wherein the tissue sample holder includes a plurality of wipers, wherein each wiper is secured to the shaft such that each wiper extends radially outwardly from the shaft.

Example 4

The core needle biopsy device of Example 2, wherein the tissue sample holder includes a single wiper extending radially outwardly from the shaft.

Example 5

The core needle biopsy device of Example 1, wherein the tissue sample holder further includes a base, wherein the base includes a plurality of sidewalls and a floor defining the sample chamber, wherein the wiper is secured to the base, wherein the base is configured to translate relative to the piercer to translate the wiper relative to the piercer and thereby manipulate a severed tissue sample into the tissue sample chamber.

Example 6

The core needle biopsy device of Example 5, wherein the base further includes a manipulator, wherein the manipulator is in communication with the drive mechanism such that the drive mechanism is configured to drive translation of the base relative to the piercer.

Example 7

The core needle biopsy device of Example 6, wherein the manipulator includes a plurality of wedge-shaped manipulators.

Example 8

The core needle biopsy device of Example 6, wherein the manipulator includes a plurality of gear teeth arranged in a plurality of discrete groups.

Example 9

The core needle biopsy device of Example 6, wherein the manipulator includes a plurality of gear teeth arranged in a plurality of discrete groups, wherein the drive assembly includes an gear having an intermittent gear portion, wherein the intermittent gear portion is configured to engage the plurality of gear teeth to translate the base intermittently in response to continuous rotation of the gear.

Example 10

The core needle biopsy device of any one or more of Examples 1 through 9, further comprising a sample tray configured for receipt within a portion of the tissue sample holder, wherein the sample tray is configured to engage the wiper to manipulate a severed tissue sample from the wiper and into an interior space defined by the sample tray.

Example 11

The core needle biopsy device of Example 10, wherein the sample tray includes a collection tooth, wherein the collection tooth is configured to engage the wiper to manipulate a severed tissue sample from the wiper and into the interior space defined by the sample tray.

Example 12

The core needle biopsy device of any one or more of Examples 1 through 11, wherein the wiper includes a material having a durometer of 30 to 80.

Example 13

The core needle biopsy device of any one or more of Examples 1 through 11, wherein the wiper defines a thin substantially rectangular shape.

Example 14

The core needle biopsy device of any one or more of Examples 1 through 11, wherein the wiper defines a curved edge configured to atraumatically engage tissue.

Example 15

The core needle biopsy device of any one or more of Examples 1 through 14, further comprising a body having a distal end, wherein the needle assembly extends distally from the distal end of the body, wherein the tissue sample holder is disposed on the distal end of the body.

Example 16

A tissue sample holder for use with a core needle biopsy device, wherein the core needle biopsy device includes piercer having a sample notch and a cutter movable relative to the sample notch to sever a tissue sample, wherein the tissue sample holder comprises: an body defining a sample chamber; and at least one wiper movable relative to a portion of the tissue sample holder to manipulate a severed tissue sample from the sample notch of the piercer and into the sample chamber of the body.

Example 17

The tissue sample holder of Example 16, further comprising a rotatable shaft, wherein the wiper extends radially outwardly from the shaft, wherein the body includes a cylindrical inner wall defining the sample chamber, wherein the wiper is configured to slide along the inner wall of the body to move a severed tissue sample within the sample chamber.

Example 18

The tissue sample holder of Example 17, wherein the wiper defines a curved portion, wherein the curved portion defines a curvature oriented in a direction corresponding to a rotation direction of the shaft.

Example 19

The tissue sample holder of Example 17, wherein the wiper is secured to the body such that the body is configured to move the wiper relative to the piercer.

Example 20

A method for collecting a tissue sample using a biopsy device, the method comprising: retracting a sample notch defined by a piercer proximally into a tissue sample holder; moving a wiper within the tissue sample holder to sweep the wiper across the sample notch; further moving the wiper away from the sample notch and towards a sample chamber.

Example 21

The method of Example 20, wherein the act of moving the wiper includes rotating the wiper using a shaft coupled to the wiper.

Example 22

The method of Example 21, wherein the wiper is a first wiper, the method further comprising rotating the shaft to move a second wiper within the tissue sample holder to sweep the second wiper across the sample notch.

Example 23

The method of Example 20, wherein the act of moving the wiper incudes translating the wiper by translating a base coupled to the wiper.

Example 24

The method of any one or more of Examples 20 through 23, further comprising moving the wiper to sweep the wiper across a collection tooth of a tissue tray.

Example 25

The method of any one or more of Examples 20 through 24, wherein the acts of moving the wiper both include using the wiper to manipulate a tissue sample.

Example 26

A biopsy device, comprising: a body defined by a probe and a holster; a needle assembly extending distally from the probe, wherein the needle assembly is configured to sever a tissue sample; and a tissue sample holder having a sample chamber and a wiper, wherein the wiper is movable relative to a portion of the needle assembly to manipulate a severed tissue sample into the sample chamber.

Example 27

The biopsy device of Example 26, wherein the tissue sample holder includes a rotatable shaft, wherein the wiper is secured to the shaft such that rotation of the shaft is configured to rotate the wiper relative to a portion of the needle assembly to thereby manipulate a severed tissue sample into the sample chamber.

Example 28

The biopsy device of Example 27, wherein the tissue sample holder includes a plurality of wipers, wherein each wiper is secured to the shaft such that each wiper extends radially outwardly from the shaft.

Example 29

The biopsy device of Example 27, wherein the tissue sample holder includes a single wiper extending radially outwardly from the shaft.

Example 30

The biopsy device of Example 26, wherein the tissue sample holder further includes a base, wherein the base includes a plurality of sidewalls and a floor defining the sample chamber, wherein the wiper is secured to the base, wherein the base is configured to translate relative to the needle assembly to translate the wiper relative to the needle assembly and thereby manipulate a severed tissue sample into the tissue sample chamber.

Example 31

The biopsy device of Example 30, further comprising a drive mechanism, wherein the base further includes a manipulator, wherein the manipulator is in communication with the drive mechanism such that the drive mechanism is configured to drive translation of the base relative to the needle assembly.

Example 32

The biopsy device of Example 31, wherein the manipulator includes a plurality of wedge-shaped manipulators.

Example 33

The biopsy device of Example 31, wherein the manipulator includes a plurality of gear teeth arranged in a plurality of discrete groups.

Example 34

The biopsy device of Example 31, wherein the manipulator includes a plurality of gear teeth arranged in a plurality of discrete groups, wherein the drive assembly includes an gear having an intermittent gear portion, wherein the intermittent gear portion is configured to engage the plurality of gear teeth to translate the base intermittently in response to continuous rotation of the gear.

Example 35

The biopsy device of any one or more of Examples 26 through 34, further comprising a sample tray configured for receipt within a portion of the tissue sample holder, wherein the sample tray is configured to engage the wiper to manipulate a severed tissue sample from the wiper and into an interior space defined by the sample tray.

Example 36

The biopsy device of Example 35, wherein the sample tray includes a collection tooth, wherein the collection tooth is configured to engage the wiper to manipulate a severed tissue sample from the wiper and into the interior space defined by the sample tray.

Example 37

The biopsy device of any one or more of Examples 26 through 36, wherein the wiper includes a material having a durometer of 30 to 80.

Example 38

The biopsy device of any one or more of Examples 26 through 36, wherein the wiper defines a thin substantially rectangular shape.

Example 39

The biopsy device of any one or more of Examples 26 through 36, wherein the wiper defines a curved edge configured to atraumatically engage tissue.

Example 40

The biopsy device of any one or more of Examples 26 through 39, wherein the probe has a distal end, wherein the needle assembly extends distally from the distal end of the probe, wherein the tissue sample holder is disposed on the distal end of the probe.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

We claim:

1. A core needle biopsy device, comprising:

(a) a needle assembly including a piercer and a hollow cutter, the piercer being solid and defining a longitudinal piercer axis, the piercer including a sharp distal tip and defining a notch proximal to the distal tip, the notch being a cutout laterally disposed along a solid portion of the needle such that the solid portion extends an entire length of the notch, the piercer being slidably disposed within the cutter to sever a tissue sample into the notch of the piercer;

(b) a drive assembly configured to selectively move the piercer and the cutter; and (c) a tissue sample holder having a sample chamber and a wiper, the wiper defining a tissue manipulation portion, the wiper being flexible, the wiper being movable about a wiper axis and relative to the piercer and cutter to manipulate a severed tissue sample into the sample chamber, the wiper being configured to sweep the tissue manipulation portion across the entire length of the notch and to move within the sample chamber to push the severed tissue sample out of the notch and into the sample chamber, the longitudinal piercer axis and the wiper axis being parallel.

2. The core needle biopsy device of claim 1, the tissue sample holder including a rotatable shaft, the wiper being secured to the shaft such that rotation of the shaft is configured to rotate the wiper relative to the piercer to thereby manipulate a severed tissue sample into the sample chamber.

3. The core needle biopsy device of claim 2, the tissue sample holder including a plurality of wipers, which includes the wiper, each wiper of the plurality of wipers being secured to the shaft such that each wiper of the plurality of wipers extends radially outwardly from the shaft.

4. The core needle biopsy device of claim 2, wherein the wiper is a single wiper extending radially outward from the shaft.

5. The core needle biopsy device of claim 1, the tissue sample holder further including a base, the base including a plurality of sidewalls and a floor defining the sample chamber, the wiper being secured to the base, the base being configured to translate relative to the piercer to translate the wiper relative to the piercer and thereby manipulate a severed tissue sample into the tissue sample chamber.

6. The core needle biopsy device of claim 5, the base further including a manipulator, the manipulator being in communication with the drive assembly such that the drive assembly is configured to drive translation of the base relative to the piercer.

7. The core needle biopsy device of claim 6, the manipulator including a plurality of wedge-shaped manipulators.

8. The core needle biopsy device of claim 6, the manipulator including a plurality of gear teeth arranged in a plurality of discrete groups.

9. The core needle biopsy device of claim 6, the manipulator including a plurality of gear teeth arranged in a plurality of discrete groups, the drive assembly including a gear having an intermittent gear portion, the intermittent gear portion being configured to engage the plurality of gear teeth to translate the base intermittently in response to continuous rotation of the gear.

10. The core needle biopsy device of claim 1, further comprising a sample tray configured for receipt within a portion of the tissue sample holder, the sample tray being configured to engage the wiper to manipulate a severed tissue sample from the wiper and into an interior space defined by the sample tray.

11. The core needle biopsy device of claim 10, the sample tray including a collection tooth, the collection tooth being configured to engage the wiper to manipulate a severed tissue sample from the wiper and into the interior space defined by the sample tray.

12. The core needle biopsy device of claim 1, the wiper including a material having a durometer of 30 to 80.

13. The core needle biopsy device of claim 1, the wiper defining a thin rectangular shape.

14. The core needle biopsy device of claim 1, the wiper defining a curved edge configured to atraumatically engage tissue.

15. The core needle biopsy device claim 1, further comprising a body having a distal end, the needle assembly extending distally from the distal end of the body, the tissue sample holder being disposed on the distal end of the body.

16. A tissue sample holder for use with a core needle biopsy device, the core needle biopsy device including a piercer having a sample notch and a cutter movable relative to the sample notch to sever a tissue sample, the tissue sample holder comprising:

(a) a body defining a sample chamber; and (b) at least one wiper movable through the sample chamber of the tissue sample holder to manipulate a severed tissue sample from the sample notch of the piercer and into the sample chamber of the body.

17. The tissue sample holder of claim 16, further comprising a rotatable shaft, the at least one wiper extending radially outwardly from the shaft, the body including a cylindrical inner wall defining the sample chamber, the at least one wiper being configured to slide along the inner wall of the body to move a severed tissue sample within the sample chamber.

18. The tissue sample holder of claim 17, the at least one wiper defining a curved portion, the curved portion defining a curvature oriented in a direction corresponding to a rotation direction of the shaft.

19. The tissue sample holder of claim 17, the at least one wiper being secured to the body such that the body is configured to move the at least one wiper relative to the piercer.

20. A method for using a biopsy device, the method comprising:

(a) retracting a sample notch defined by a piercer proximally into a tissue sample holder;

(b) rotating a wiper relative to the sample notch and within the tissue sample holder to thereby sweep the wiper across the sample notch; and (c) after rotating the wiper to thereby sweep the wiper across the sample notch, moving the wiper away from the sample notch and towards a sample chamber.

* * * * *